(12) United States Patent
Heaton et al.

(10) Patent No.: US 8,084,628 B2
(45) Date of Patent: Dec. 27, 2011

(54) SUBSTITUTED CHROMAN DERIVATIVES, MEDICAMENTS AND USE IN THERAPY

(75) Inventors: Andrew Heaton, Abbotsford (AU); Alan Husband, McMahon's Point (AU)

(73) Assignee: Marshall Edwards, Inc., San Diego, CA (US)

( * ) Notice: Subject to any disclaimer, the term of this patent is extended or adjusted under 35 U.S.C. 154(b) by 0 days.

(21) Appl. No.: 12/551,277

(22) Filed: Aug. 31, 2009

(65) Prior Publication Data

US 2009/0317490 A1   Dec. 24, 2009

Related U.S. Application Data

(62) Division of application No. 11/230,726, filed on Sep. 21, 2005, now Pat. No. 7,601,855.

(60) Provisional application No. 60/611,300, filed on Sep. 21, 2004, provisional application No. 60/676,934, filed on May 3, 2005.

(30) Foreign Application Priority Data

Nov. 19, 2004   (WO) ............... PCT/AU2004/001619

(51) Int. Cl.
*C07D 311/00* (2006.01)
*A61K 35/32* (2006.01)
*A01N 43/02* (2006.01)
*A01N 43/16* (2006.01)

(52) U.S. Cl. ......... 549/403; 424/549; 514/449; 514/456

(58) Field of Classification Search .................. 549/403; 424/549; 514/449, 456

See application file for complete search history.

(56) References Cited

U.S. PATENT DOCUMENTS

| | | | |
|---|---|---|---|
| 3,340,276 A | 9/1967 | Carney | |
| 3,471,520 A | 10/1969 | Irmscher et al. | |
| 3,535,344 A | 10/1970 | Irmscher | |
| 4,157,984 A | 6/1979 | Zilliken | |
| 4,218,489 A | 8/1980 | Zilliken | |
| 4,232,122 A | 11/1980 | Zilliken | |
| 4,234,577 A | 11/1980 | Zilliken | |
| 4,366,082 A | 12/1982 | Zilliken | |
| 4,366,248 A | 12/1982 | Zilliken | |
| 4,368,264 A | 1/1983 | Zilliken | |
| 4,390,559 A | 6/1983 | Zilliken | |
| 4,447,622 A | 5/1984 | Salman et al. | |
| 4,814,346 A | 3/1989 | Albert et al. | |
| 5,059,609 A | 10/1991 | Eggler et al. | |
| 5,280,040 A | 1/1994 | Labroo et al. | |
| 5,389,646 A | 2/1995 | Labroo | |
| 5,464,862 A | 11/1995 | Labroo et al. | |
| 5,696,149 A | 12/1997 | Korsgaard et al. | |
| 5,726,202 A | 3/1998 | Shalmi et al. | |
| 5,756,539 A | 5/1998 | Skrumsager et al. | |
| 5,780,503 A | 7/1998 | Biftu et al. | |
| 5,849,461 A | 12/1998 | Hatakeyama et al. | |
| 5,883,118 A | 3/1999 | Shalmi et al. | |
| 5,919,817 A * | 7/1999 | Jacobsen et al. | 514/456 |
| 5,958,967 A | 9/1999 | Jacobsen et al. | |
| 5,985,306 A * | 11/1999 | Jacobsen et al. | 424/423 |
| 5,994,390 A | 11/1999 | Jacobsen et al. | |
| 5,998,451 A | 12/1999 | Eggler et al. | |
| 6,005,003 A | 12/1999 | Nique | |
| 6,043,269 A | 3/2000 | Jacobsen et al. | |
| 6,316,494 B1 | 11/2001 | Jacobsen et al. | |
| 6,610,733 B2 | 8/2003 | Park et al. | |
| 6,645,951 B1 | 11/2003 | Jo et al. | |
| 6,649,648 B1 | 11/2003 | Kelly et al. | |
| 7,056,952 B1 | 6/2006 | Joannon | |
| 7,202,273 B2 | 4/2007 | Kelly et al. | |
| 7,601,855 B2 | 10/2009 | Heaton | |
| 2009/0317490 A1 | 12/2009 | Heaton | |

FOREIGN PATENT DOCUMENTS

| | | |
|---|---|---|
| EP | 313295 A2 | 4/1989 |
| EP | 0470310 A1 | 12/1992 |
| EP | 0267155 A2 | 5/1998 |
| EP | 0955286 | 11/1999 |
| GB | 1433013 | 4/1976 |
| JP | 2000-506507 | 5/2000 |
| JP | 2001-502706 | 2/2001 |
| JP | 2001-502711 | 2/2001 |
| WO | WO-80-02098 A1 | 10/1980 |
| WO | 94/08986 A1 | 4/1994 |
| WO | 94/20099 A1 | 9/1994 |
| WO | 96/21442 A1 | 7/1996 |
| WO | 96/21443 A1 | 7/1996 |
| WO | 96/21444 A1 | 7/1996 |
| WO | 96/22091 A1 | 7/1996 |
| WO | 96/22092 A1 | 7/1996 |
| WO | 96/22093 A1 | 7/1996 |
| WO | 97/25035 A1 | 7/1997 |
| WO | 97/25036 A1 | 7/1997 |
| WO | WO-97-25038 A1 | 7/1997 |

(Continued)

OTHER PUBLICATIONS

B. Aggarwal, et al., "From chemoprevention to chemotherapy: common targets and common goals", Expert Opin. Investig. Drugs, (2004), vol. 13(10): pp. 1327-1338.

T. Akimoto, et al., "Genistein, a tyrosine kinase inhibitor, enhanced radiosensitivity in human esophageal cancer cell lines in vitro: possible involvement of inhibition of survival signal transduction pathways", Int. J. Radiation Oncology Biol. Phys., vol. 50, No. 1, pp. 195-201, 2001.

F. Bellisarii, et al., "Tumor necrosis factor-α and cardiovascular diseases", Ital Heart J 2001; vol. 2(6): pp. 408-417.

(Continued)

*Primary Examiner* — Nizal Chandrakumar
(74) *Attorney, Agent, or Firm* — Wilson, Sonsini, Goodrich & Rosati

(57) ABSTRACT

Novel substituted chroman derivatives and intermediate compounds, compositions containing same, methods for their preparation and uses thereof as therapeutic agents particularly as anti-cancer and chemotherapeutic selective agents are described.

13 Claims, 1 Drawing Sheet

FOREIGN PATENT DOCUMENTS

| | | |
|---|---|---|
| WO | 98/02154 A1 | 1/1998 |
| WO | 98/02156 A1 | 1/1998 |
| WO | WO-98-08503 A1 | 3/1998 |
| WO | 98/17662 A1 | 4/1998 |
| WO | 98/18770 A1 | 5/1998 |
| WO | 98/18771 A1 | 5/1998 |
| WO | 98/18778 A1 | 5/1998 |
| WO | WO-98-18772 A1 | 5/1998 |
| WO | WO-98-18773 A1 | 5/1998 |
| WO | WO-98-18774 A1 | 5/1998 |
| WO | WO-98-18775 A1 | 5/1998 |
| WO | WO-98-18776 A1 | 5/1998 |
| WO | WO-98-18778 A1 | 5/1998 |
| WO | WO-98-18779 A1 | 5/1998 |
| WO | 98/25916 A1 | 6/1998 |
| WO | 98/32437 A1 | 7/1998 |
| WO | 98/33499 A1 | 8/1998 |
| WO | 98/33500 A1 | 8/1998 |
| WO | 99/49862 A1 | 10/1999 |
| WO | 99/55898 A1 | 11/1999 |
| WO | 99/63974 A2 | 12/1999 |
| WO | 99/65893 A1 | 12/1999 |
| WO | WO-00-66576 A1 | 11/2000 |
| WO | 01/17986 A1 | 3/2001 |
| WO | 01/26651 A2 | 4/2001 |
| WO | 01/54699 A1 | 8/2001 |
| WO | 02/02548 A1 | 1/2002 |
| WO | 02/059113 A1 | 8/2002 |
| WO | 03/016270 A2 | 2/2003 |
| WO | 03/035635 A1 | 5/2003 |
| WO | 03/063859 A1 | 8/2003 |
| WO | 03/086386 A1 | 10/2003 |
| WO | 2004/030662 A1 | 4/2004 |
| WO | 2005/049008 A1 | 6/2005 |
| WO | 2006/032085 A1 | 3/2006 |
| WO | 2006/032086 A1 | 3/2006 |

OTHER PUBLICATIONS

B. Bradbury, "Some oestrogenic 4-phenyl-substituted isoflav-3-ENS", Australian Journal of Chemistry, vol. 6, 1953, pp. 447-449.

P. Bury, et al., "Synthesis and pharmacological evaluation of novel cis-3,4-diaryl-hydroxychromanes as high affinity partial agonists for the estrogen receptor", Bioorganic & Medicinal Chemistry, vol. 10, (2002), pp. 125-145.

A. Constantinou, et al., "Phenoxodiol, a novel isofavone derivative, inhibits dimethylbenz[a]anthracene(DMBA)-induced mammary carcinogenesis in female Sprague—Dawley rats", European Journal of Cancer, vol. 39, (2003), pp. 1012-1018.

A. Constantinou, et al. "Phenoxodiol (2H-1-Benzopyran-7-0,1,3-(4-hydroxyphenyl), a Novel Isoflavone Derivative, Inhibits DNA Topoisomerase II by Stabilizing the Cleavable Complex", Anticancer Research, vol. 22, pp. 2581-2586, (2002).

T. Dorai, et al., "Role of chemopreventive agents in cancer therapy" Cancer Letters, vol. 215, (2004), pp. 129-140.

J. Gamble, et al., "Phenoxodiol, an experimental anticancer drug, shows potent antiangiogenic properties in addition to its antitumour effects", Int. J. Cancer, vol. 118, pp. 2412-2420, (2006).

P. Hersey, et al., "How melanoma cells evade trail-induced apoptosis" Nov. 2001, vol. 1, pp. 142-150.

Hem Chandra Jha, et al., "Carbon -13- chemical shift assignments of chromones and isoflavones", Can, J. Chem., vol. 58, pp. 1211-1219, (1980).

Y. Kakeji, et al., "Preclinical studies of the combination of angiogenic inhibitors with cytotoxic agents" Investigational New Drugs, vol. 15, pp. 39-48, 1997.

M. Kamsteeg, et al., "Phenoxodiol—an isoflavone analog- induces apoptosis in chemoresistant ovarian cancer cells" Oncogene, (2003), vol. 22, pp. 2611-2620.

B. Kang, et al., "Scientific Analysis of Formulation Theory of Chungpesagan- tang; In vitro Cytotoxicity of Cisplatin Combined with Chungpesagan-tang", Natural Product Sciences, vol. 6(4), pp. 165-169, (2000).

S. Khoshyomn, et al., "Synergistic Action of Genistein and Ciplatin on Growth Inhibition and Cytotoxicity of Human Medulloblastoma Cells"; Pediatr. Neurosurg. 2000, vol. 33, pp. 123-131.

Y. Li, et al., "Apoptosis-Inducing Effect of Chemotherapeutic Agents Is Potentiated by Soy Isoflavone Genistein, a Natural Inhibitor of NF-KB in BxPC-3 Pancreatic Cancer Cell Line", Pancreas, vol. 28, No. 4, pp. e90-e95, date unavailable.

C. McDonnell, et al., "Improvement in Efficacy of Chemoradiotherapy by Addition of and Antiangiogenic Agent in a Murine Tumor Model", Journal of Surgical Research, Vo. 116, pp. 19-23, (2004).

R. Micheli, et al., "Coumestro, Plant Phenolics, and Synthetic Estrogens: a Correlation of Structure and Activity", Journal of Medicinal and Pharmaceutical Chemistry, vol. 5, 1962, pp. 321-335.

Nakata, E. et al., "C225 Antiepidermal Growth Factor Receptor Antibody Enhances the Efficacy of Docetaxel Chemoradiotherapy", Int. J. Radiation Oncology Biol. Phys., vol. 59, No. 4, pp. 1163-1173, 2004.

P. O'Dwyer, et al., "Antitumor Activity and Biochemical Effects of Aphidicolin Glycinate(NSC 303812) Alone and in Combination with Cisplatin in Vivo"; Cancer Research, vol. 54, pp. 724-729, Feb. 1, 1994.

M. O'Neill, et al., "Inducible Isoflavonoids from the Lima Bean, *Phaseolus lunatus*", Phytochemistry, vol. 25, No. 6, pp. 1315-1322, 1986.

M. Rafi, et al., "Modulation of bcl-2 and Cytotoxicity by Licochalcone-A, a Novel Estrogenic Flavonoid", Anticancer Research, vol. 20, pp. 2653-2658, (2000).

M. Ravindranath, et al., "Anticancer Therapeutic Potential of Soy Isoflavone, Genistein", Complementary and Alternative Approaches to Biomedicine, edited by Edwin L. Cooper and Nobuo Yamaguchi. Kluwer Academic/Plenum Publishers, 2004, p. 121.

S. Sepulveda-Boza, et al., "The preparation of new isoflavones", Synthetic Communications, vol. 3(12), pp. 1933-1940, (2001).

P. Szlosarek, et al., "Tumour necrosis factor $\alpha$: a potential target for the therapy of solid tumours", The Lancet Oncology, vol. 4, pp. 565-573, Sep. 2003.

S. Tamura, et al., "Genistein Enhances the Cisplatin-Induced Inhibition of Cell Growth and Apoptosis in Human Malignant Melanoma Cells"; Pigment Cell Res., vol. 16, pp. 470-476, 2003.

P. Todorov, et al., "Role of a proteolysis-inducing factor(PIF) in a cachexia induced by a human melanoma(G361)", British Journal of Cancer, (1999), vol. 80(11), pp. 1734-1737.

Verma, P. et al., "Smooth Conversion of 3,4-Diarylcoumarins and 3,4,5- Triaryl-2(5H)-furanones to 2H-Chromene and 2,5-Dihydrofuran Derivatives with Dimethyl Sulfide-Borane Complex", Synthesis, vol. 1, 1988, pp. 68-70.

W. Lei, et al., "Enhancement of Chemosensitivity and Programmed Cell death by Tyrosine Kinase Inhibitors Correlates with EGFR Expression in Non-Small Cell Lung Cancer Cells", Anticancer Research, vol. 19, pp. 221-228, (1989).

O. Wolfbeis, et al., "The Absorption and Fluorescence of Isoflavones and the Effect of Shift Reagents", Z. Naturforsch, vol. 39b, pp. 238-243, (1984); received Sep. 23, 1983.

E. Zyner, et al., "Platinum(II) and palladium(II) N,0-Chelates with substituted flavanone containing ligangs", Acta Polonia Pharmaceutica, Drug Research, vol. 56, No. 2, pp. 159-167, 1999.

E. Zyner, et al., "Pt(II) and Pd(II) complexes of 3-aminoflavone: In vitro and in vivo evaluation", Pharmazie, 54, (1999), 12, pp. 945-946.

B. Abegaz, et al., "Isoflavonoids from the roots of Salsola somalensis", Phytochemistry (1991), vol. 30(4), pp. 1281-1284.

V. Agarwal, et al., "Phenolic constituents of Iris Milesii rhizomes", Phytochemistry (Elsevier) (1984), vol. 23(6), pp. 1342-1343.

V. Agarwal, et al.,"Isoflavones of two Iris species", Phytochemistry (Elsevier) (1984), vol. 23(11), pp. 2703-2704.

S. Antus, et al., "Synthesis of some pterocarpenes obtained from Brya ebenus", J. Chem. Soc., Perkin Trans, (1982), vol. 6, pp. 1389-1394.

A. Arnone, et al., "Isoflavonoid constituents of the West African red wood, Baphia nitida", Phtyochemistry (1981), vol. 20(4), pp. 799-801.

B. Bezuidenhoudt, "Synthesis of isoflavanoid oligomers using a pterocapan as inceptive electrophile"; Journal of the Chemical Society, Perkin Transactions 1: Organic and Bio-Organic Chemistry (1972-1999), (1984), vol. 12, pp. 2767-2778.

K. Briviba, et al., "Isoflavonoids as inhibitors of lipid peroxidation and quenchers of singlet oxygen", Antioxidants in Health and Disease(1998), 7(Flavonoids in Health and Disease), pp. 295-302.

S. Caltagirone, et al., "Flavanoids apigenin and quercetin inhibit melanoma growth and metastatic potential", International Journal of Cancer, (Aug. 15, 2002), vol. 87(4), pp. 595-600.

S. Caltagirone, et al., "Interaction with type II estrogen binding sites and antiproliferative activity of tamoxifen and quercetin in human non-small-cell lung cancer", American Journal of Respiratory Cell and Molecular Biology, (Jul. 1997), vol. 17 (1), pp. 51-59.

R. De Vincenzo, et al.,"Flavanoids and negative control of cell proliferation in ovarian tumors", Acta Medica Romana (1992), vol. 30(1-2), pp. 126-132.

K. Fukui, et al., "The synthesis of irisolone", Bull. Chem. Soc. Japan (1965), vol. 38(6), pp. 887-893.

S. Giacomelli. et al., "Silybin and its bioavailable, phospholipid complex(IdB 1016) potentiate in vitro and in vivo the activity of cisplatin", Life Sciences, (Feb. 8, 2002), vol. 70 (12), pp. 1447-1459.

S. Gupta et al., "The use of Friedel-Crafts reactions for the synthesis of deoxybenzoins", Indian J. Chem. (1968), vol. 6(9), pp. 481-484.

T. Horie, et al.,"Studies of the selective O-alkylation and dealkylation of flavonoids. XX. A convenient method for synthesizing 5,6,7-trihydroxyisoflavones and 5,6-dihydroxy-7-methoxyisoflavones", Chemical & Pharmaceutical Bulletin, (1996), Vo. 44(3), pp. 486-491.

H. Ito, et al., "Isoflavonoids from Belamcanda chinensis", Chemical & Pharmaceutical Bulletin,.(2001), vol. 49 (9), pp. 1229-1231.

J. Kinjo, et al., "Novel santalin analogs from Pterpcarpus santalinus (leguminosae): their biogenesis and anti-oxidative activities", Tennen Yuki Kagobutsu Toronkai Koen Yoshishu, (1995), 37th, pp. 493-498.

K. Klus, et al., "Formation of polyhydroxylated isoflavones from the soybean seed isoflavones daidzein and glycitein by bacteria isolated from tempe", Archives of Microbiology (1995), vol. 164(6, pp. 428-434.

H. Kothari, et al., "Inhibition of cholesterol ester transfer protein by CGS 25159 and changes in lipoproteins in hamsters", Atherosclerosis (Shannon, Ireland) (1997), vol. 128(1), pp. 59-66.

S. E. Kulling, et al., "Oxidative metabolism of the soy isoflavones daidzein and genistein in humans in vitro and in vivo", Journal of Agricultural and Food Chemistry (2001), vol. 49(6), pp. 3024-3033.

W. Lawson, "Estrogenic activity of some derivatives of isoflaven and isoflavanol", Journal of the Chemical Society, (1954), pp. 4448-4450.

N. V. Mani, et al, "Isoflavones. III. Nitration of 7,8- and 6,7-dihydroxyisoflavones and their methyl ether", J. Inst. Chem., Calcutta (1971), vol. 43(6), pp. 234-240.

N. V. Mani, et al., "Isoflavones. I. Bromination of isoflavones", J. Inst. Chem., Calcutta (1974), vol. 46, Pt.3, pp. 61-65.

A. Mansour, et al., "Enhancement of Chemotherapeutic Efficacy by Combining Agents that Block IL-10 in CLL Cell Lines", New Jersey Medical School, UMDNJ, Newark, NJ, USA Blood, (Nov. 16, 2002) vol. 100, No. 11, pp. Abstract No. 4997. print.

J. B. Montandon, et al.,"In-vitro versus in-vivo activities of new 5-lipoxygenase inhibitors with anti-inflammatory activity", International Journal of Tissue Reactions, (1989), vol. 11(3), pp. 107-112.

S. S. Neelam, et al., "Combination of flavone acetic acid (FAA) with adriamycin, cis-platinum and diflouoromethylornithine (DFMO) in vitro against human colon cancer cells", Investigational New Drugs, (Aug. 1990) vol. 8(3), pp. 263-268.

G. Scambia, et al., "Antiproliferative effect of silybin on gynaecological malignancies;synergism with cisplatin and doxorubicin", European Journal of Cancer, (May 1996), vol. 32A (5), pp. 877-882.

G. Scambia, "Synergistic antiproliferative activity of quercetin and cisplatin on ovarian cancer cell growth", Anti-Cancer Drugs, (Oct. 1990), vol. 1(1), pp. 45-48.

T. Shingo, et al., "Genistein enhances the cisplatin—induced inhibition of cell growth and apoptosis in human malignant melanoma cells", Pigment Cell Research, (Oct. 2003), vol. 16 (5), pp. 470-476.

C. C. Teo, et al., "Synthesis of 3-(p-fluorophenyl)-4-arylchrom-3-enes as selective ligands for antiestrogen-binding sites", Journal of Chemical Research, Synopses, (1990), vol. 1, pp. 4-5.

C. C. Teo, et at., "Synthesis of arylchromenes and arylchromans", Bulletin of the Singapore National Institute of Chemistry, (1994), vol. 22, pp. 69-74.

J. Varady, "The flavonoids of Podocarpus spicatus. I. Structure of podospicatin. Synthesis of podospicatin mono-,di-, and trimethyl ethers", Periodica Polytech., (1963), vol. 7(4), pp. 241-258.

C. Voss, et al., "New isoflavonoids as inhibitors of porcine 5-lipoxygenase", Biochemical Phamacology, (1992), vol. 44(1),pp. 157-162.

W. R. Waud, et al., "Antitumor drug cross-resistance in vivo in a cisplatin-resistant murine P388 leukemia", Cancer Chemotherapy and Pharmacology, (1991), vol. 27 (6), pp. 456-463.

M. Weidenborner, et al., "Control of storage fungi of the genus Aspergillus on legumes with flavonoids and isoflavonoids", *Angewandte botanik*, (1990), vol. 64 (1-2), pp. 175-190.

Registration No. 143358-39-8, 4H-1-Benzopyran-4-one, 2,3-dihydro-7-methoxy-3-(4-methoxyphenyl)-(−) (9CI), Sep. 9, 1992.

Registration No. 143358-24-1, 4H-1-Benzopyran-4-one, 2,3-dihydro-7-methoxy-3-(4-methoxyphenyl)-(+)-(9CI), Sep. 9, 1992.

Registration No. 15236-11-0, 4H-1-Benzopyran-4-one, 2,3-dihydro-7-methoxy-3-(4-methoxyphenyl)-(9CI), Nov. 16, 1984.

Registration No. 67492-31-3, 4H-1-Benzopyran-4-one, 2,3-dihydro-7-hydroxy-3-(3-hydroxy-4-methoxyphenyl)-(9CI), Nov. 16, 1984.

Registration No. 304892-19-1, 4H-1-Benzopyran-4-one, 3-(3,4-dihydroxyphenyl)-2,3-dihydro-7-hydroxy-(9CI), Nov. 29, 2000.

Registration No. 206257-38-7, 4H-1-Benzopyran-4-one, 2,3-dihydro-3-(4-hydroxyphenyl)-7-methoxy-(9CI), Jun. 3, 1998.

Registration No. 83206-83-1, 4H-1-Benzopyran-4-one, 3-(3,4-dimethoxyphenyl)-2,3-dihydro-7-hydroxy-(9CI), Nov. 16, 1984.

Registration No. 124093-18-1, 4H-1-Benzopyran-4-one, 2,3-dihydro-7-hydroxy-3-(4-hydroxy-3-methoxyphenyl)-(9CI), Dec. 1, 1989.

Registration No. 95307-73-6, 4H1-Benzopyran-4-one-2-d, 2,3-dihydro-2-d-7-hydroxy-3-(4-methoxyphenyl)-(9CI), Mar. 16, 1985.

Registration No. 4626-22-6, 4H-1-Benzopyran-4-one, 2,3-dihydro-7-hydroxy-3-(4-methoxyphenyl)-(9CI), Nov. 16, 1984.

Registration No. 143358-39-8, 4H-1-Benzopyran-4-one, 2,3-dihydro-7-methoxy-3-(4-methoxyphenyl)-(−)-(9CI), Sep. 9, 1992.

Registration No. 201678-33-3, 4H-1-Benzopyran-4-one, 3-(3,4-dimethoxyphenyl)-2,3-dihydro-7,8-dimethoxy-(9CI), Feb. 22, 1998.

Registration No. 116703-40-3, 4H-1-Benzopyran-4-one, 2,3-dihydro-7,8-dimethoxy-3-(4-methoxyphenyl)-(9CI), Oct. 2, 1988.

Registration No. 206257-38-7, 4H-1-Benzopyran-4-one, 2,3-dihydro-3-(4-hydroxyphenyl)-7-methoxy-(9CI), Jun. 3, 1998.

Registration No. 680195-83-9, 4H-1-Benzopyran-4-one, 2,3-dihydro-7,8-dihydroxy-3-(4-hydroxyphenyl)-(9CI), May 6, 2004.

Registration No. 129159-04-2, 4H-1-Benzopyran-4-one, 2,3-dihydro-3-(4-hydroxyphenyl)-(9CI), Aug. 31, 1990.

Registration No. 116703-49-2, 4H-1-Benzopyran-4-one, 2,3-dihydro-7,8-dihydroxy-3-(4-methoxyphenyl)-(9CI), Oct. 2, 1988.

Registration No. 39604-72-3, 4H-1-Benzopyran-4-one, 2,3-dihydro-7methoxy-3-(4-methoxyphenyl)-8-methyl-(9CI), Nov. 16, 1984.

Registration No. 129159-05-3, 4H-1-Benzopyran-4-one, 3-(3,4-dihydroxyphenyl)-2,3-dihydro-(9CI), Aug. 31, 1990.

Registration No. 95307-73-6, 4H-1-Benzopyran-4-one-2-d, 2,3-dihydro-2-d-7-hydroxy-3-(4-methoxyphenyl)-(9CI), Mar. 16, 1985.

Registration No. 36282-40-3, Magnesium, bromo(3-methoxyphenyl)-, Nov. 16, 1984.

Registration No. 16750-63-3, Magnesium, bromo(2-methoxyphenyl)-(9CI), Nov. 16, 1984.

Registration No. 13139-86-1, Magnesium, bromo(4-methoxyphenyl)-(9CI), Nov. 16, 1984.

Registration No. 142050-44-0, 4H-1-Benzopyran-4-one, 7-hydroxy-3-[4-methoxy-3-(methoxy-t3)phenyl]-(9CI), Jun. 26, 1992.

Registration No. 95457-39-9, 4H-1-Benzopyran-4-one-4-14C, 3-(3,4-dimethoxyphenyl)-7-hydroxy-(9CI), Mar. 23, 1985.

Registration No. 24160-14-3, 4H-1-Benzopyran-4-one, 3-(3,4-dimethoxyphenyl)-7-hydroxy-(9CI), Nov. 16, 1984.

Registration No. 288267-24-3, 4H-1-Benzopyran-4-one, 7-hydroxy-3-(4-hydroxy-3-methoxyphenyl)-8-methyl-(9CI), Sep. 6, 2000.

Registration No. 116718-51-5, 4H-1-Benzopyran-4-one, 7-hydroxy-3-(4-methoxyphenyl)-8-methyl-methyl-(9CI), Oct. 2, 1988.

Registration No. 1157-39-7, 4H-1-Benzopyran-4-one, 7-methoxy-3-(4-methoxyphenyl)-methyl-(9CI), Nov. 16, 1984.
Registration No. 85915-64-6, 2H-1-Benzopyran-7-ol, 4-[5-(3,4-dihydro-7-hydroxy-2-H-1-benzopyran-3-yl)-4-hydroxy-2-methoxyphenyl]-3,4-dihydro-3-(2-hydroxy-4-methoxyphenyl)-,[3S-[3α-4β(R)]]-(9CI), date unavailable.
Registration No. 95541-42-7, 1,3-Benzenediol, 4-[3,4-dihydro-3-(2-hydroxy-4-methoxyphenyl)-7-methoxy-2H-1-benzopyran-4-yl]-,(3R-trans)-(9CI), date unavailable.
Registration No. 95541-44-9, 1,3,5-Benzenetriol,2-[3,4-dihydro-3-(2-hydroxy-4-methoxyphenyl)-7-methoxy-2H-1-benzopyran-4-yl]-,(3R-trans)-(9CI), date unavailable.
Registration No. 95541-45-0, 1,3,5-Benzenetriol,2,4-bis[3,4-dihydro-3-(2-hydroxy-4-methoxyphenyl)-7-methoxy-2H-1-benzopyran-4-yl]-,[3R-[3α,4β(3R,4S)]]-(9CI), date unavailable.
Registration No. 95541-51-8, 2H-1-Benzopyran-7-ol,3-[-[3,4-dihydro-3-(2-hydroxy-4-methoxphenyl)-7-methoxy-2H-1-benzopyran-4-yl]-2-hydroxy-4-methoxyphenyl]-3,4-dihydro-,[3R-3α,4β(S)]]-(9CI), date unavailable.
Registration No. 95541-54-1, 2H-1-Benzopyran-7-ol,3,4-dihydro-4-[4-hydroxy-5-(7-hydroxy-2H-1-benzopyran-3-yl)-2-methoxyphenyl]-3-(2-hydroxy-4-methoxyphenyl)-(3S-trans)-(9CI), date unavailable.
Registration No. 85915-66-8, 2H-1-Benzopyran,4-[5-(3,4-dihydro-7-methoxy-2H-1-benzopyran-3-yl)-2,4-dimethoxyphenyl]-3-(2,4-dimethoxyphenyl)-3,4-dihydro-7-methoxy-,[3S-[3α4β(R)]]-(9CI), date unavailable.
Registration No. 95541-43-8, 2H-Benzopyran,3,4-bis(2,4-dimethoxyphenyl)-3,4-dihydro-7-methoxy-,(3R-trans)-(9CI), date unavailable.
Registration No. 95541-46-1, 2H-1-Benzopyran,3-(2,4-dimethoxyphyenyl)-3,4-dihydro-7-methoxy-4(2,4,6-trimethoxyphenyl)-,(3R-trans)-(9CI), date unavailable.
Registration No. 95541-53-0, 2H-1-Benzopyran,4-[5(3,4-dihyrdro-7-methoxy-2H-1-benzopyran-3-yl)-2,4-dimethoxyphenyl]-3-(2,4-dimethoxyphenyl)-3,4-dihydro-7-methoxy-,[3R-[3α,4β(S)]]-(9CI), date unavailable.
95541-57-4, 2H-1-Benzopyran,4-[2,4-dimethoxy-5-(7-methoxy-2H-1-benzopyran-3-yl)phenyl]-3-(2,4-dimethoxyphenyl)-3,4-dihydro-7-methoxy-,(3S-trans)-(9CI), date unavailable.
Registration No. 95541-66-5, 2H-1-Benzopyran,4-(2,4-dimethoxyphenyl)-3,4-dihydro-7-methoxy-3-[4-methoxy-2-(methoxymethoxy)phenyl]-,(3R-trans)-(9CI), date unavailable.
Registration No. 95762-78-0, 2H-1-Benzopyran,4,4'-(2,4,6-trimethoxy-1,3-phenylene)bix[3-(2,4-dimethoxyphenyl)-3,4-dihydro-7-methoxy-,[3R[3α,4β(3'R,4'S)]]-(9CI), date unavailable.
Aldrich Handbook of Fine Chemicals and Laboratory Equipment (c) 2002, Sigma-Aldrich Pty Limited, Australia: Note: Sigma-Aldrich is a US Company, catalogue/handbook from which the pages derive from is the AU publication.
Gamble, Jr., Xia, P., Hahn, C.,, Drew, J., Drogemuller, C., Brown, DM., Vadas, MA, 2006, Int. J. Cancer, 118, 2412-2420 (2006).
Bezuidenhoudt et al., "Synthesis of Isoflavanoid Oligomers Using a Pterocarpan as Inceptive Electrophile," J Chem Soc Parkin Trans 1:2767-2778 (1984).
EP05787045.3 Search Report dated Oct. 7, 2008.
EP05779877.9 Search Report dated Apr. 28, 2009.

* cited by examiner

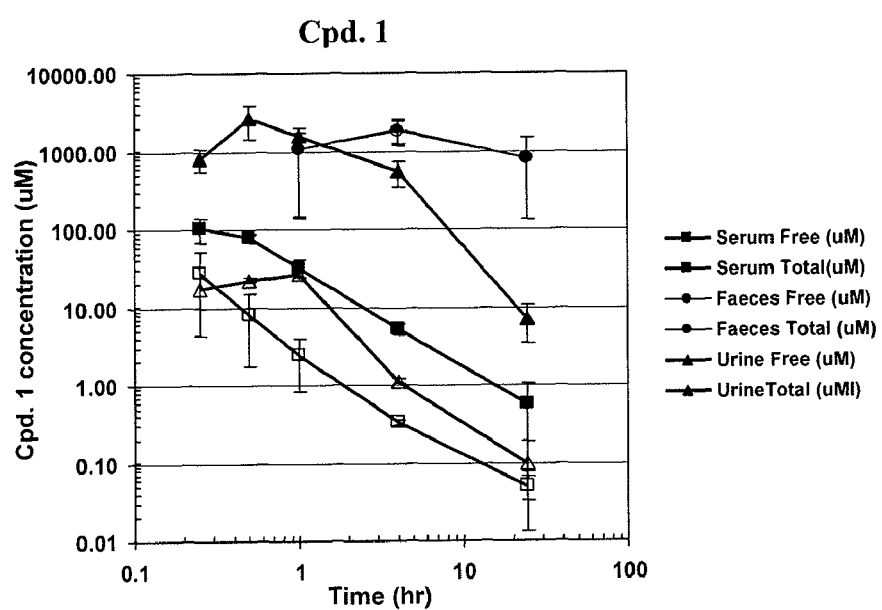
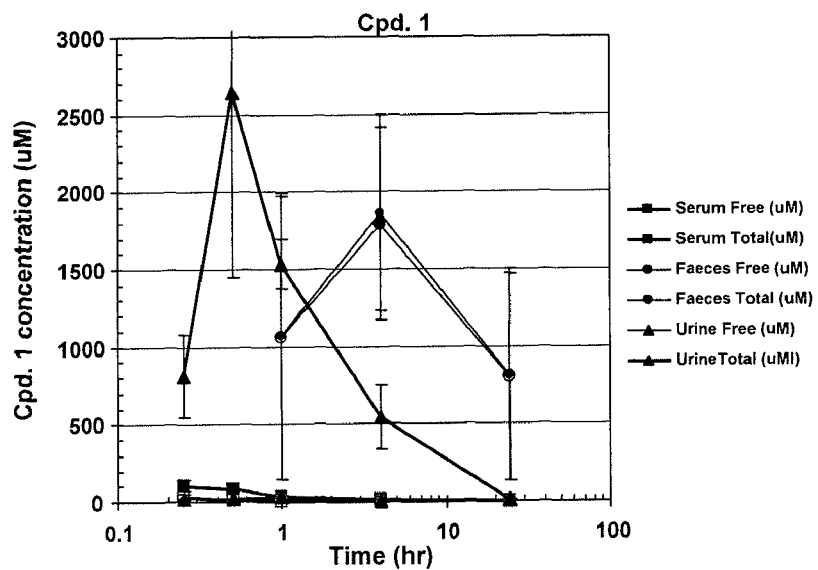

SUBSTITUTED CHROMAN DERIVATIVES, MEDICAMENTS AND USE IN THERAPY

CROSS-REFERENCE

This is a divisional of application Ser. No. 11/230,726, filed Sep. 21, 2005, which claims benefit of Provisional Application Ser. No. 60/611,300, filed Sep. 21, 2004, and Provisional Application Ser. No. 60/676,934, filed May 3, 2005, and claims priority to International Application No. PCT/AU2004/001619, filed Nov. 19, 2004, the entire disclosures of said prior applications are hereby incorporated by reference.

FIELD OF THE INVENTION

The present invention relates to certain novel chroman derivatives and their salts and derivatives, compositions containing same, methods for their preparation and uses thereof as therapeutic agents particularly as anti-cancer and chemotherapeutic selective agents.

BACKGROUND OF THE INVENTION

Over 700 different naturally occurring isoflavones are known some of which have biological properties with potential therapeutic benefit.

U.S. Pat. No. 5,726,202 generically discloses certain isoflavan compounds, particularly 3,4-diarylchroman and centchroman for the treatment of benign prostatic hypertrophy.

WO 01/17986 also discloses certain isoflavan compounds.

SUMMARY OF THE INVENTION

Surprisingly, the present inventors have found a novel group of compounds of the general formula (I) which exhibit important therapeutic activities including strong anti-cancer activity, chemotherapeutic selectivity and radiosensitisation of cancers.

Thus according to an aspect of the present invention there is provided a compound of the general formula (I):

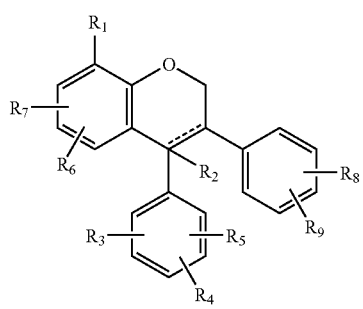

(I)

or a salt or derivative thereof wherein:

$R_1$ is hydrogen, hydroxy, halo, $NR_{10}R_{11}$, $C_{3-6}$ cycloalkyl, $C_{1-6}$ alkoxy, $C_{2-6}$ alkenyl, $C_{1-6}$ fluoroalkyl or $C_{1-6}$ alkyl optionally substituted by one or more hydroxy, chloro, bromo, iodo or $NR_{10}R_{11}$ groups;

the drawing "---" and $R_2$ together represent a double bond or the drawing "---" represents a single bond and $R_2$ is hydrogen, hydroxy, $NR_{10}R_{11}$, $C_{1-3}$ alkoxy, $C_{1-3}$ fluoroalkyl, halo or $C_{1-3}$ alkyl optionally substituted by one or more hydroxy, chloro, bromo, iodo or $NR_{10}R_{11}$ groups;

$R_3$ is hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, $(O)_nC_{1-4}$ alkyleneNR$_{14}$R$_{15}$ or $C_{1-6}$ alkyl optionally substituted by one or more hydroxy, chloro, bromo, iodo or $NR_{10}R_{11}$ groups;

$R_4$, $R_5$, $R_6$, $R_7$, $R_8$ and $R_9$ are independently hydrogen, hydroxy, halo, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$ or $C_{1-6}$ alkyl optionally substituted by one or more hydroxy, chloro, bromo, iodo or $NR_{10}R_{11}$;

$R_{10}$, $R_{11}$ and $R_{12}$ are independently hydrogen, $C_{1-6}$ alkyl, $C_{3-6}$ cycloalkyl or trialkyl silyl;

$R_{13}$ is hydrogen, $C_{1-6}$ alkyl, $C_{3-6}$ cycloalkyl or $NR_{10}R_{11}$;

n represents 0 or 1; and $R_{14}$ and $R_{15}$ independently represent hydrogen or $C_{1-6}$ alkyl or $NR_{14}R_{15}$ when taken together represents a 5 or 6 member heteroaromatic or heterocyclic;

and pharmaceutically acceptable salts thereof, with the proviso that when $R_1$ represents hydrogen and "---" is a single bond then $R_2$ does not represent hydrogen.

According to another aspect of the present invention there is provided a process for the preparation of a compound of formula (I).

According to another aspect of the present invention there is provided a pharmaceutical composition which comprises one or more compounds of formula (I) or a pharmaceutically acceptable salt or derivative thereof in association with one or more pharmaceutical carriers, excipients, auxiliaries and/or diluents.

Thus, according to another aspect of the present invention there is provided the use of a compound of formula (I) in therapy, particularly chemotherapy and as radiosensitising agents.

According to another aspect of the present invention there is provided a method for the treatment, prevention or amelioration of a disease or disorder, which comprises administering to a subject an effective amount of one or more compounds of the formula (I) or a pharmaceutically acceptable salt or derivative thereof optionally in association with a carrier and/or excipient.

According to another aspect of the present invention there is provided an agent for the treatment, prophylaxis or amelioration of a disease or disorder which agent comprises one or more compounds of formula (I) or a pharmaceutically acceptable salt or derivative thereof.

BRIEF DESCRIPTION OF THE FIGURE

FIG. 1. Shows pharmacokinetics and distribution of compound No. 1 identified below in serum, faeces and urine. Average values are presented for free and total concentrations of the compound (±SEM) as a semi-log plot in part A and as a standard linear plot in part B.

DETAILED DESCRIPTION OF THE INVENTION

The present inventors have found that compounds of the general formula (I) show surprising and unexpected biological and pharmaceutical properties.

The compounds of formula (I) of the invention are believed to have favourable toxicity profiles with normal cells and good bioavailability. Surprisingly the compounds of the invention exhibit anti-cancer activity, significantly better than or at least comparable to known cancer treatments.

The compounds of formula (I) are cytostatic and cytotoxic against a broad range of cancer cells of human and animal origin. By cancer cells, it is meant cells that display malignant characteristics and which are distinguished from non-cancer cells by unregulated growth and behaviour which usually ultimately is life-threatening unless successfully treated.

The cancer cells that have been found to be responsive to compounds of formula (I) are of epithelial origin (for example, prostate, ovarian, cervical, breast, gall-bladder, pancreatic, colorectal, renal, and non-small lung cancer cells), of mesenchymal origin (for example, melanoma, mesothelioma and sarcoma cancer cells), and of neural origin (for example glioma cancer cells).

It is highly unusual and surprising to find a related group of compounds that display such potent cytotoxicity against cancer cells. Furthermore it is thought that the compounds according to the invention also have low toxicity against non-cancer cells such as keratinocytes derived from human foreskin. Such cancer cell selectivity is highly unusual and unexpected.

Advantageously the compounds of formula (I) show cytotoxicity against cancer cells that are well recognised for being poorly sensitive to standard anti-cancer drugs. It is highly unusual and unexpected to find such potent activity against cancers, for example, cholangiocarcinoma, pancreatic adenocarcinoma and melanoma, that are highly resistant to known anti-cancer drugs.

Advantageously the compounds of formula (I) also seem to display an ability to radio-sensitise cancer cells, by which it is meant that these compounds either lower the amount of gamma-irradiation that is required to kill the cells, or they convert cancer cells from a state of radio-resistance to radio-sensitivity.

Additionally the compounds of formula (I) are thought to possess chemo-sensitising activity, that is they increase the cytotoxicity of chemotherapeutic agents, especially to cancer cells, and/or convert cancerous cells from a state of chemo-resistance to a chemo-sensitive state.

Compounds of the invention may also provide chemo and/or radio-protective properties for non-cancerous cells. This has significant therapeutic implications because the traumatic side-effects of chemotherapy and radiotherapy are caused by the toxicity of the traditional treatments to non-cancerous cells.

The properties described above offer significant clinical advantages.

The radio and/or chemo-protective properties of the compounds of the invention may be employed to protect healthy individuals from the effects of radiation and/or chemical toxins, or lessen the effects of the same.

The properties described above offer significant clinical advantages.

The invention also provides the use of compounds of formula (I) to treat patients with cancer by either reducing the rate of growth of such tumours or by reducing the size of such tumours through therapy with such compounds alone, and/or in combination with each other, and/or in combination with other anti-cancer agents, and/or in combination with radiotherapy.

Generally in compounds of formula (I) according to the invention the substituents $R_8$ and $R_9$ will be distributed as shown below:

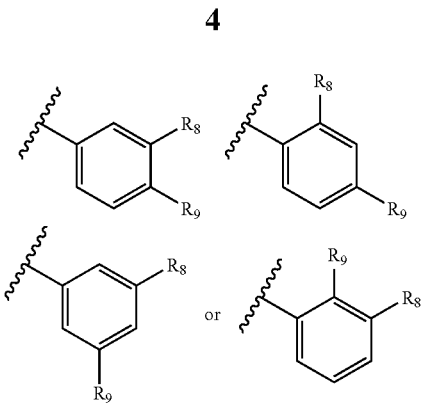

Generally in compounds of formula (I) according to the invention the substituents $R_3$, $R_4$ and $R_5$ will be distributed as shown below:

Preferably in compounds of formula (I) the drawing "---" represents a single bond.

Preferably in compounds of the invention, including compounds of formula (I) $R_3$ will be in the para-position.

In compounds of the invention, including compounds of formula (I) when $R_3$ represents $(O)_nC_{1-4}$ alkyleneNR$_{14}$R$_{15}$ preferably it represents —OC$_2$ alkyleneNR$_{14}$R$_{15}$ wherein NR$_{14}$R$_{15}$ represents pyrrolidinyl.

According to the invention there is provided compounds of formula (I-a):

(I-a)

or a salt or derivative thereof wherein
$R_1$, $R_2$, $R_3$, $R_4$, $R_5$, $R_6$, $R_7$ and $R_8$ are as defined above for compounds of formula (I)
with the proviso that when $R_1$ represents hydrogen and "---" is a single bond then $R_2$ does not represent hydrogen.

The positions of $R_3$, $R_4$ and $R_5$ shown above for compounds of formula (I) apply equally to compounds of formula (I-a).

The position of $R_8$ and $R_9$ shown above for compounds of formula (I) equally applies to compounds of formula (I-a).

In compounds of formula (I-a) $R_7$ preferably represents $C_{1-6}$ alkoxy or hydroxy, especially methoxy or hydroxy.

In compounds of formula (I-a) preferably "---" represents a single bond.

In another preferred aspect the invention there is provided compounds of formula (I-b):

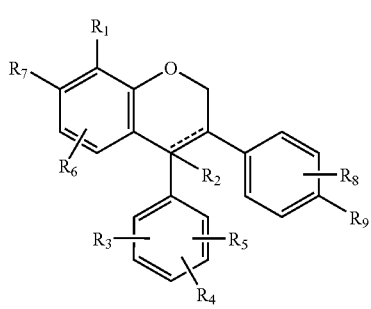
(I-b)

or a salt or derivative thereof wherein $R_1$ represents hydroxy, halo, $NR_{10}R_{11}$, $C_{3-6}$ cycloalkyl, $C_{-6}$ alkoxy, $C_{2-6}$ alkenyl, $C_{1-6}$ fluoroalkyl, $C_{1-6}$ alkyl optionally substituted by one or more hydroxy, chloro, bromo, iodo or $NR_{10}R_{11}$ groups; and $R_3$, $R_4$, $R_5$, $R_6$, $R_7$, $R_8$ and $R_9$ are defined above for compounds of formula (I).

The positions of $R_3$, $R_4$ and $R_5$ shown above for compounds of formula (I) apply equally to compounds of formula (I-b).

The position of $R_8$ and $R_9$ shown above for compounds of formula (I) apply equally to compounds of formula (I-b).

Preferably in compounds of formula (I-b) $R_1$ represents hydroxy, $C_{1-6}$ alkoxy, $C_{1-6}$ fluoroalkyl, $C_{1-6}$ alkyl optionally substituted by one or more hydroxy, chloro, bromo, iodo or $NR_{10}R_{11}$ groups, especially $C_{1-6}$ alkyl, particularly methyl.

Preferably in compounds of formula (I-b) $R_3$ represents hydroxy, $C_{1-6}$ alkoxy or $C_{1-6}$ alkyl optionally substituted by one or more hydroxy, chloro, bromo, iodo or $NR_{10}R_{11}$ groups, especially $C_{1-6}$ alkoxy or hydroxy, particularly methoxy.

Preferably in compounds of formula (I-b) $R_3$ is in the para position.

Preferably in compounds of formula (I-b) $R_4$, $R_5$ and $R_6$ independently represents hydrogen.

Preferably in compounds of formula (I-b) $R_7$ represents hydroxy or $C_{1-6}$ alkoxy, especially hydroxy or methoxy.

Preferably in compound of formula (I-b) $R_8$ represents hydrogen, hydroxy or $C_{1-6}$ alkoxy, especially hydrogen, hydroxy or methoxy, particularly hydrogen.

Preferably in compounds of formula (I-b) $R_8$ is in the 3 position.

Preferably $R_9$ in compounds of formula (I-b) represents hydrogen hydroxy or $C_{1-6}$ alkoxy, especially hydroxy or $C_{1-6}$ alkoxy, particularly hydroxy or methoxy.

Thus, in another aspect the invention provides compounds of the formula (I-bb):

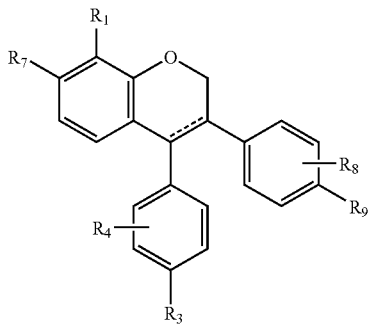
(I-bb)

or a salt or derivative thereof wherein $R_1$, $R_3$, $R_4$, $R_7$, $R_8$ and $R_9$ are as defined above for compounds of formula (I-b).

In a highly preferred embodiment, "---" represents a single bond.

The preferences expressed above for compounds of formula (I-b) apply equally to compounds of formula (I-bb).

Specific compounds within the scope of this first aspect of the invention are as follows:

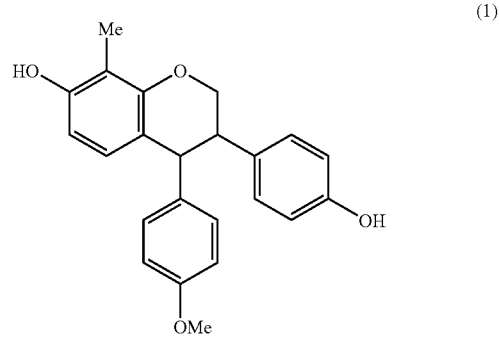
(1)

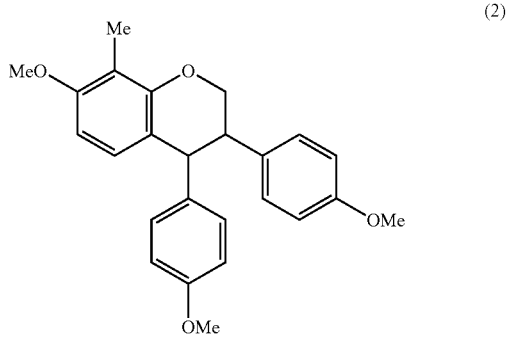
(2)

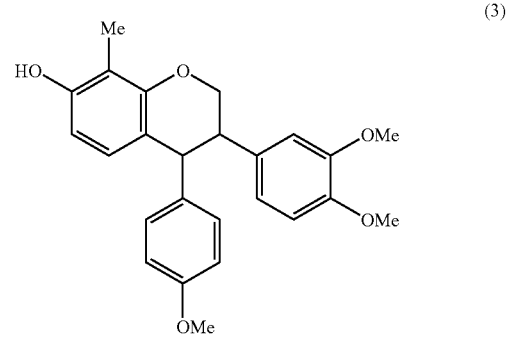
(3)

(4)
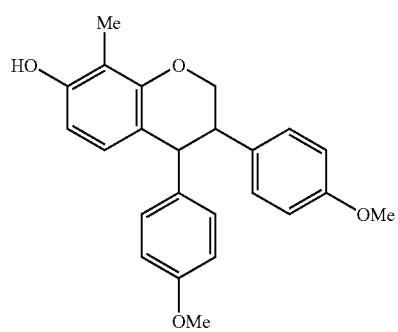
(5)
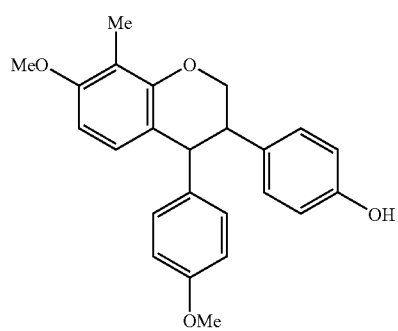
(6)
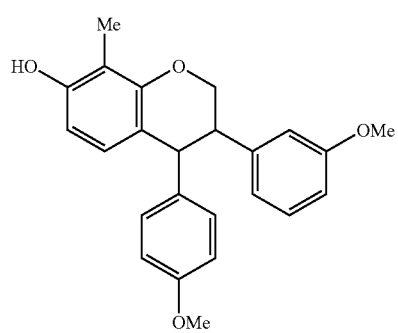
(7)
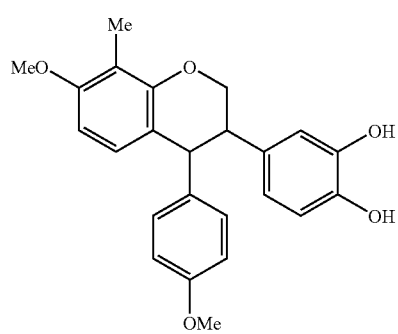
(8)
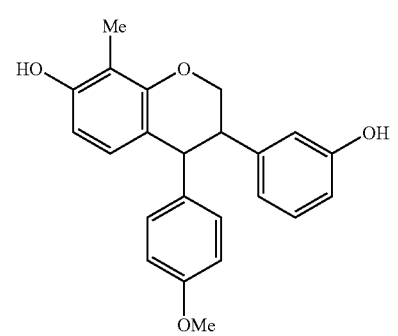
(9)
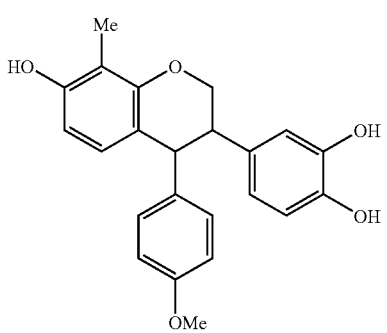
or a salt or derivative thereof.
Most preferably the compounds of formula (I-bb) have the following structure:
(1.1)
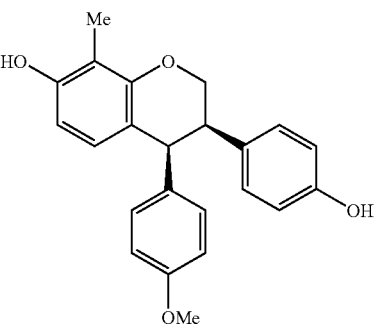
(2.1)
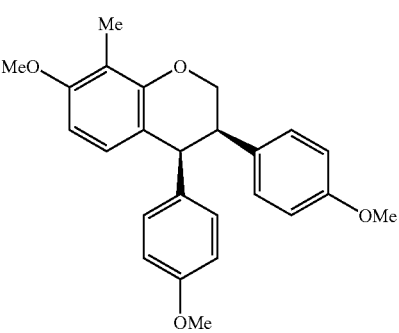
(3.1)
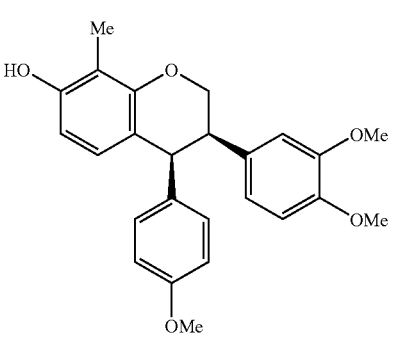
or salts or derivatives thereof.
In another preferred aspect the invention provides a compound of formula (I-c):

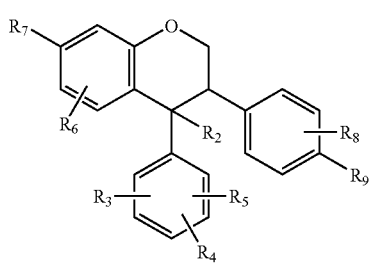

(I-c)

or a salt or derivative thereof wherein $R_2$ represents hydroxy, halo, $NR_{10}R_{11}$, $C_{1-3}$ alkoxy, $C_{1-3}$ fluoroalkyl, $C_{1-3}$ alkyl optionally substituted by one or more hydroxy, chloro, bromo, iodo or $NR_{10}R_{11}$ groups; and $R_3$, $R_4$, $R_5$, $R_6$, $R_7$, $R_8$ and $R_9$ are as defined above for compounds of formula (I).

The positions of $R_3$, $R_4$ and $R_5$ shown above for compounds of formula (I) apply equally to compounds of formula (I-b).

The position of $R_8$ and $R_9$ shown above for compounds of formula (I), where $R_9$ is in the para position apply equally to compounds of formula (I-b). $NR_{10}R_{11}$ in compounds of formula (I-c) preferably represents hydrogen or $C_{1-3}$ alkyl, especially hydrogen or methyl.

Preferably in compounds of formula (I-c) $R_2$ represents hydroxy, methoxy, methyl or trifluoromethyl.

Preferably in compounds of formula (I-c) $R_3$ represents hydroxy, $C_{1-6}$ alkoxy or $C_{1-6}$ alkyl optionally substituted by one or more hydroxy, chloro, bromo, iodo or $NR_{10}R_{11}$ groups, especially $C_{1-6}$ alkoxy, such as methoxy, particularly methoxy. Preferably in compounds of formula (I-c) $R_4$, $R_5$ and $R_6$ independently represent hydrogen.

Preferably in compounds of formula (I-c) $R_8$ represents hydrogen, hydroxy or $C_{1-6}$ alkoxy, more preferably hydrogen or methoxy, especially hydrogen.

Preferably in compounds of formula (I-c) $R_8$ is situated in the 3 position.

Preferably in compounds of formula (I-c) $R_9$ represents, hydrogen, hydroxy or $C_{1-6}$ alkoxy, especially hydroxy or $C_{1-6}$ alkoxy, particularly hydroxy or methoxy.

More preferably in this second aspect the invention provides a compound of formula (I-cc):

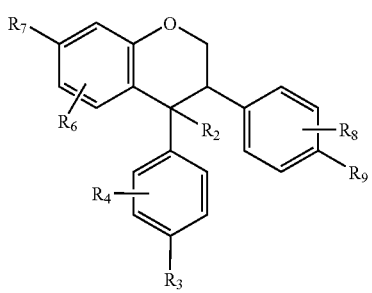

(I-cc)

or a salt or a derivative thereof wherein:

$R_2$, $R_3$, $R_4$, $R_6$, $R_7$, $R_8$ and $R_9$ are defined above for compounds of formula (I-c).

Preference expressed above for compounds of formula (I-c) apply equally to compound of formula (I-cc).

Specific compounds of formula (I-cc) are shown below:

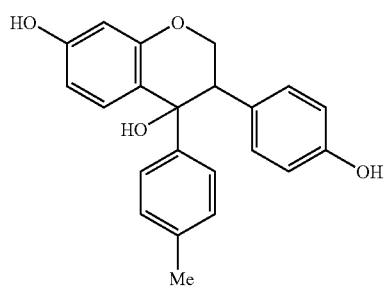

(10)

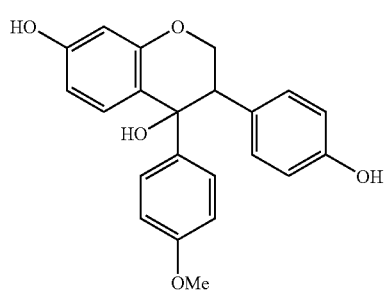

(11)

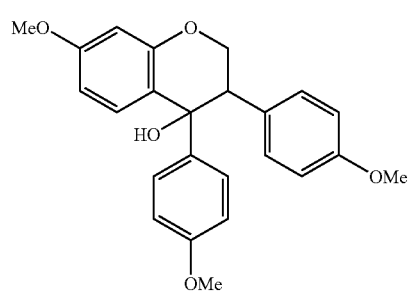

(12)

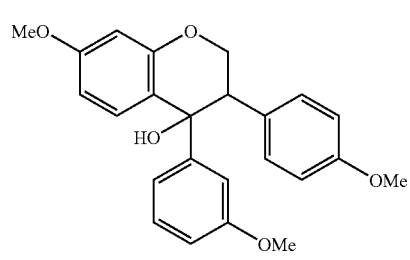

(13)

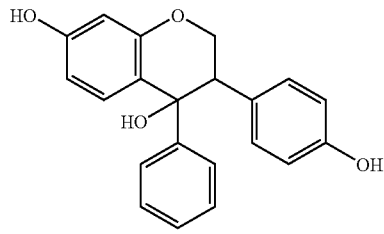

(14)

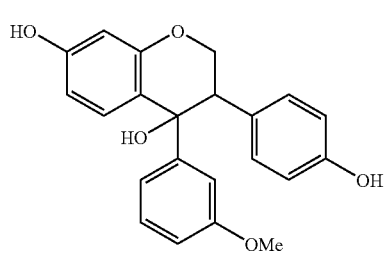

(15)

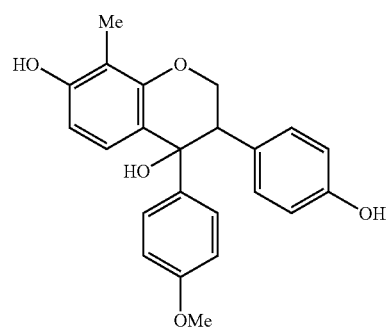
(16)
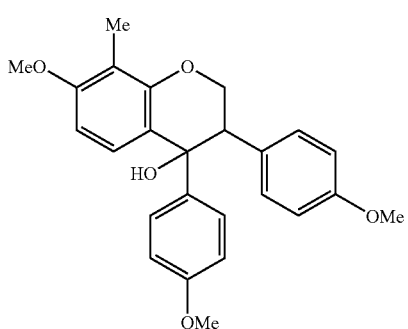
(17)
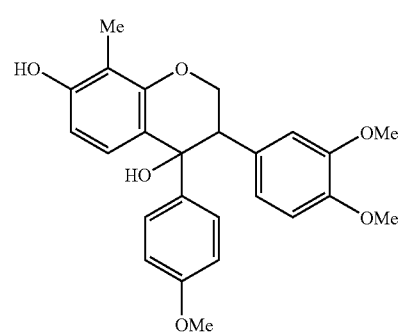
(18)
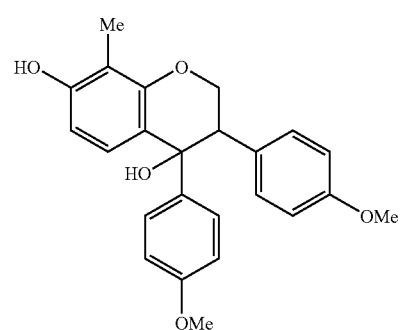
(19)
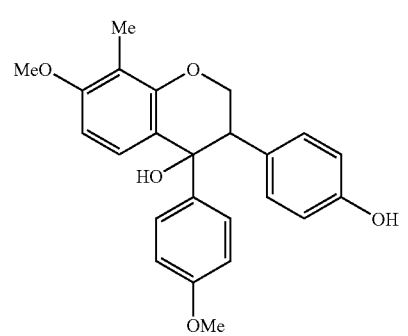
(20)
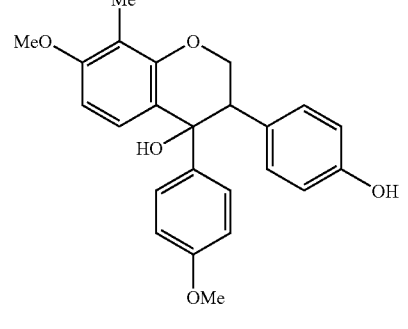
(21)
(22)
(23)
(24)
(25)
or a salt or a derivative thereof.
The compounds of formula (I) according to the invention include two chiral centers. The present invention includes all the enantiomers and diastereoisomers as well as mixtures thereof in any proportions. The invention also extends to isolated enantiomers or pairs of enantiomers. Methods of separating enantiomers and diastereoisomers are well known to person skilled in the art.

It will be clear to persons skilled in the art that in the compounds according to the invention the aryl substituents on the heterocyclic ring can be cis or trans relative to each other. Preferably in the compounds according to the invention of formula (I) these substituents will be cis.

A particularly preferred compound of the present invention is the cis-isomer of compound labelled compound No. 1 above.

Likewise, particularly preferred compounds are compound Nos. (2) to (9) in the cis-conformation.

Preferably, the salts of compounds according to the invention will be pharmaceutically acceptable salts.

The term alkyl is taken to include straight chain and branched chain saturated alkyl groups of 1 to 6 carbon atoms, such as methyl, ethyl, propyl, isopropyl, butyl, isobutyl, sec-butyl, tertiary butyl, pentyl and the like. The alkyl group more preferably contains preferably from 1 to 4 carbon atoms, especially methyl, ethyl, propyl or isopropyl.

Cycloalkyl includes $C_{3-6}$ cycloalkyl such as cyclopropyl, cyclobutyl, cyclopentyl and cyclohexyl.

The alkyl group or cycloalkyl group may optionally be substituted by one or more of fluorine, chlorine, bromine, iodine, carboxyl, $C_{1-4}$ alkoxycarbonyl, $C_{1-4}$ alkylamino-carbonyl, di-($C_{1-4}$ alkyl)-amino-carbonyl, hydroxyl, $C_{1-4}$ alkoxy, formyloxy, $C_{1-4}$ alkyl-carbonyloxy, $C_{1-4}$ alkylthio, $C_{3-6}$ cycloalkyl or phenyl.

Preferably the alkyl group does not bear any substituents. The term $C_{1-6}$ alkoxy includes groups wherein the alkyl portion therein is a straight chain or branched chain alkyl moiety. $C_{1-6}$ alkoxy groups include: methoxy, ethoxy, propoxy, isopropoxy, butoxy, tertiary butoxy and sec-butoxy. Preferably the $C_{1-6}$ alkoxy substituents will be methoxy or ethoxy, especially methoxy.

The term fluoroalkyl includes "alkyl" wherein one or more such as 1, 2, 3, 4 or 5 of the hydrogens have been replaced by fluoro. The fluoroalkyl may be a straight chain or branched chain "alkyl" unit. Preferred fluoroalkyl groups include trifluoromethyl and pentafluoromethyl.

The term aryl is taken to include phenyl, benzyl, biphenyl and naphthyl and may be optionally substituted by one or more $C_{1-4}$ alkyl, hydroxy, $C_{1-4}$ alkoxy, carbonyl, $C_{1-4}$ alkoxycarbonyl, $C_{1-4}$ alkylcarbonyloxy, nitro or halo.

The term "halo" is taken to include fluoro, chloro, bromo and iodo, preferably fluoro, chloro.

5 or 6 membered heterocyclic and heteroaromatic rings include: pyrrole, pyrroline, pyrrolidine, oxazoline, thiazole, imidazole, imidazoline, imidazolidine, pyrazole, pyrazoline, pyrazolidine, isoxazole, isothiazole, oxadiazole, furazan, triazole, thiadiazole, pyridine, piperidine, morpholine, thiomorpholine, pyridazine, pyrimidine, pyrazine, piperazine, triazine, thiadiazone and dithiazine each of which may be optionally substituted by one or more of fluorine, chlorine, bromine, iodine, carboxyl, $C_{1-4}$ alkoxycarbonyl, $C_{1-4}$ alkylamino-carbonyl, di-($C_{1-4}$ alkyl)-amino-carbonyl, hydroxyl, $C_{1-4}$ alkoxy, formyloxy, $C_{1-4}$ alkyl-carbonyloxy, $C_{1-4}$ alkylthio or $C_{3-6}$ cycloalkyl.

The compounds of the invention include all salts, such as acid addition salts, anionic salts and zwitterionic salts, and in particular include pharmaceutically acceptable salts as would be known to those skilled in the art. The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, tosylate, citrate, bicarbonate and carbonate.

Pharmaceutically acceptable salts include those formed from: acetic, ascorbic, aspartic, benzoic, benzenesulphonic, citric, cinnamic, ethanesulphonic, fumaric, glutamic, glutaric, gluconic, hydrochloric, hydrobromic, lactic, maleic, malic, methanesulphonic, naphthoic, hydroxynaphthoic, naphthalenesulphonic, naphthalenedisulphonic, naphthaleneacrylic, oleic, oxalic, oxaloacetic, phosphoric, pyruvic, para-toluenesulphonic, tartaric, trifluoroacetic, triphenylacetic, tricarballylic, salicylic, sulphuric, sulphamic, sulphanilic and succinic acid.

The term "pharmaceutically acceptable derivative" or "prodrug" refers to a derivative of the active compound that upon administration to the recipient is capable of providing directly or indirectly, the parent compound or metabolite, or that exhibits activity itself and includes for example phosphate derivatives and sulphonate derivatives. Thus, derivatives include solvates, pharmaceutically active esters, prodrugs or the like.

The preferred compounds of the present invention also include all derivatives with physiologically cleavable leaving groups that can be cleaved in vivo to provide the compounds of the invention or their active moiety. The leaving groups may include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted compounds of the invention are readily cleavable to the corresponding hydroxy substituted compounds.

Chemical functional group protection, deprotection, synthons and other techniques known to those skilled in the art may be used where appropriate to aid in the synthesis of the compounds of the present invention, and their starting materials.

The protection of functional groups on the compounds and derivatives of the present invention can be carried out by well established methods in the art, for example as described in T. W. Greene, *Protective Groups in Organic Synthesis*, John Wiley & Sons, New York, 1981.

Hydroxyl protecting groups include but are not limited to carboxylic acid esters, eg acetate esters, aryl esters such as benzoate, acetals/ketals such as acetonide and benzylidene, ethers such as ortho-benzyl and para-methoxy benzyl ether, tetrahydropyranyl ether and silyl ethers such as tert-butyldimethyl silyl ether.

Protecting groups can be removed by, for example, acid or base catalysed hydrolysis or reduction, for example, hydrogenation. Silyl ethers may require hydrogen fluoride or tetrabutylammonium fluoride to be cleaved.

It will be clear to persons skilled in the art of medicinal chemistry that compounds of formula (I) may be converted into other compounds of formula (I), for example, where a compound of formula (I) bears one or more hydroxyl substituents then one or more of these substituents can be converted in to a halogen such as bromo, chloro or iodo by treating the alcohol with a halogenating agent, with use of protecting groups as required to protect other functionality in the molecule. Halogenating agents include compounds like NBS, hydrobromic acid and chlorine gas.

Phenolic type hydroxyls may not be readily convertible to the corresponding halogen compound by treatment with a halogenating agent. However, the desired halogen compound may be prepared by, for example, treating an appropriate aryl amine starting material with $NaNO_2$ in the presence of HCl under reduced temperature conditions such as 0° C., to form the corresponding azide salt. Subsequent treatment with CuCl, CuBr, KI or $HBF_4$ may be used to convert the azide into the required halo-compound.

A general process for preparing compounds of formula (I) comprises the steps of:

i) treating a compound of formula (II):

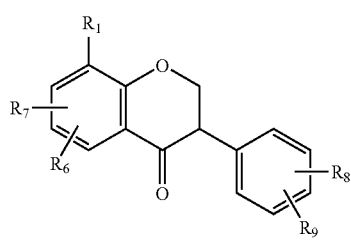

(II)

or a protected derivative thereof wherein:

$R_1$, is hydrogen, hydroxy, $NR_{10}R_{11}$, $C_{3-6}$ cycloalkyl, $C_{1-6}$ alkoxy, $C_{2-6}$ alkenyl, $C_{1-6}$ fluoroalkyl, $C_{1-6}$ alkyl optionally substituted by one or more hydroxy or $NR_{10}R_{11}$ groups; $R_6$, $R_7$, $R_8$ and $R_9$ independently represent hydrogen, hydroxy, $NR_{10}R_{11}$, $C_{3-6}$ cycloalkyl, $C_{1-6}$ alkoxy, $C_{1-6}$ fluoroalkyl, $COOR_{12}$, $COR_{13}$ or $C_{1-6}$ alkyl optionally substituted by one or more hydroxy or $NR_{10}R_{11}$ groups with a of formula (III):

(III)

or a protected derivative thereof wherein:

$R_3$ represents represents hydrogen, hydroxy, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$, $(O)_nC_{1-4}$alkyleneNR$_{14}R_{15}$, or $C_{1-6}$ alkyl optionally substituted by one or more hydroxy or $NR_{10}R_{11}$ groups;

$R_4$ and $R_5$ independently represent hydrogen, hydroxy, $NR_{10}R_{11}$, $C_{3-6}$ cycloalkyl, $C_{1-6}$ alkoxy, $C_{1-6}$ fluoroalkyl, $C_{2-6}$ alkenyl, $COOR_{12}$, $COR_{13}$ or $C_{1-6}$ alkyl optionally substituted by one or more hydroxy or $NR_{10}R_{11}$ groups; and X represents a metallohalo moiety; and ii) optionally followed by converting the tertiary alcohol group on the heterocyclic ring in the product formed to another substituent, and iii) optionally followed by deprotection.

In step i) described above the compound of formula (III) is preferably an organo metallic reagent which is reacted with the ketone compound of formula (II) under anhydrous conditions in an inert atmosphere such as under nitrogen or argon, in an inert solvent such as THF (tetrahydrofuran), at a non-extreme temperature such as room temperature, or reduced temperature, for example, 0° C.

Suitable organometallic reagents include organolithium reagents, organomagnesium reagents and organocopper reagents. More preferably the arylating agent employed is an organomagnesium reagent such as a Gringnard reagent, which may be prepared by reacting a compound of formula (III), wherein X represents halo such as bromo with magnesium metal under anhydrous conditions in an inert atmosphere.

In step ii) described above the tertiary alcohol substituent on the heterocyclic ring in the product formed from the nucleophilic addition reaction may be converted into other $R_2$ substituents by known methods. For example, treatment with para-toluenesulfonic acid can be used to convert the tertiary alcohol into a good leaving group. This intermediate tosylate may then be treated with a nucleophile such as a hydride source, an alcohol or an amine to provide the required substitution for the $R_2$ moiety.

Alternatively the tertiary hydroxyl may be converted to a halogen by use of a halogenating agent.

In a further aspect of the invention there is the dehydration of the product of said nucleophilic addition reaction to form a compound of the general formula (I-d):

(I-d)

or a protected derivative thereof wherein $R_1$, $R_3$, $R_4$, $R_5$, $R_6$, $R_7$, $R_8$ and $R_9$ are as defined above for compounds of formula (I-b).

Dehydration can, for example, be catalysed by acid, by base or facilitated by conversion of the tertiary alcohol into a better leaving group. Preferably compounds of formula (III) are dehydrated, for example, by treatment with para-toluene sulphonic acid.

Preference expressed above for compounds of formula (I-b) apply equally to compound of formula (I-d).

Specific compounds of formula (I-d) are shown below:

(26)

(27)
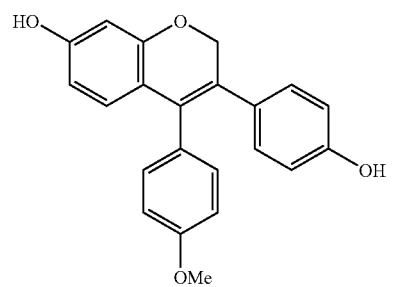
(28)
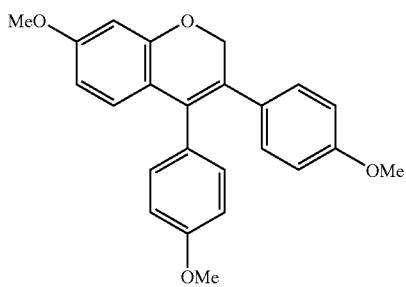
(29)
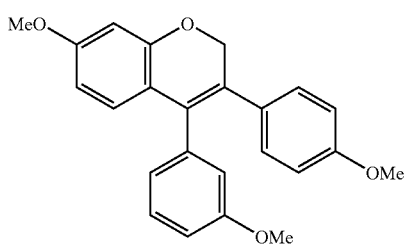
(30)
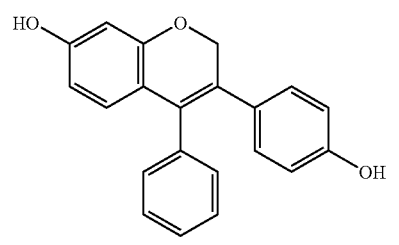
(31)
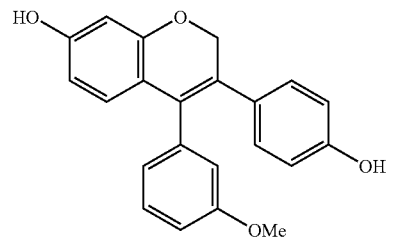
(32)
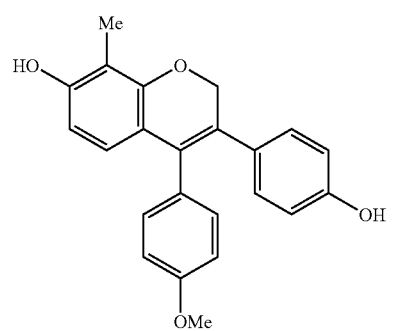
(33)
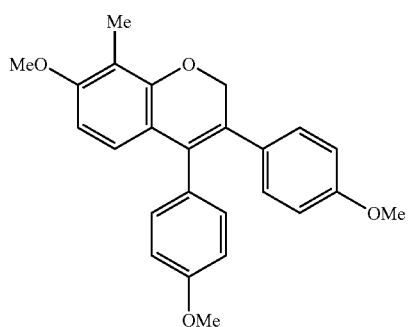
(34)
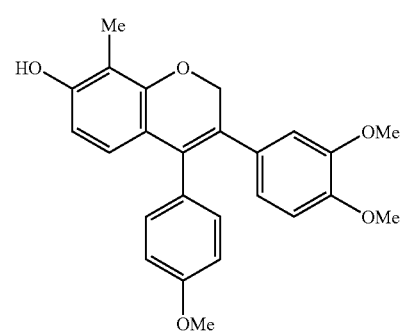
(35)
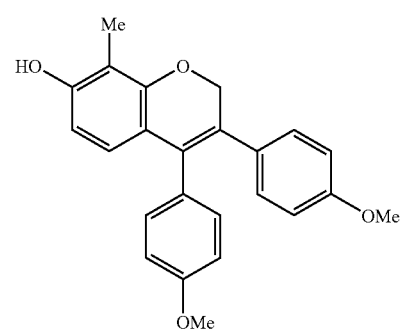
(36)
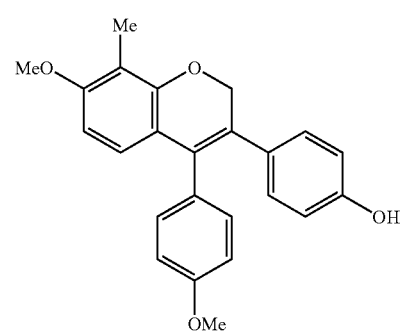
(37)
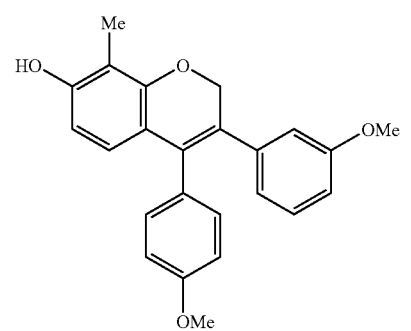

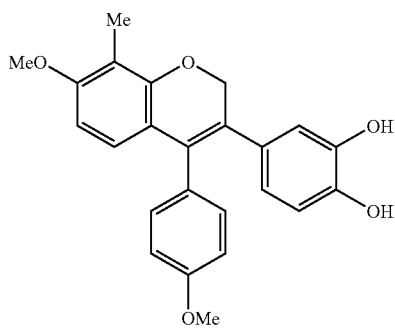
(38)

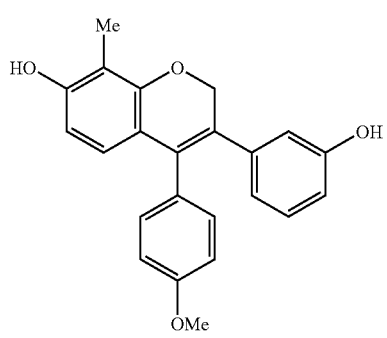
(39)

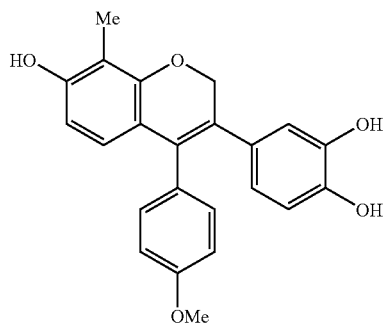
(40)

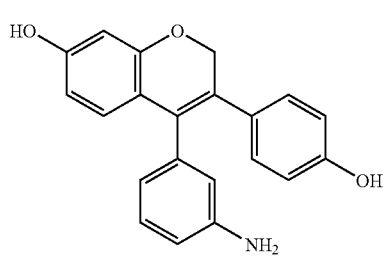
(41)

If required the double bond in the heterocycle in compounds of formula (I-d) can be removed by treatment with a reducing agent to provide other compounds of formula (I). Reducing agents are well known to persons skilled in the art and can include hydride sources like borohydrides and alkali metal borohydrides, but would include hydrogen in catalytic hydrogenation where a suitable catalyst such as palladium on carbon may be used. Other suitable hydride sources include sodium triacetoxyborohydride tetrabutyl ammonium triacetoxyborohydride and sodium cyanoborohydride.

Preferably the double bond is reduced by hydrogenation.

Compounds of formula (II) may be prepared by reducing the double bond, preferably by hydrogenation, in the heterocyclic ring in compounds of formula (IV):

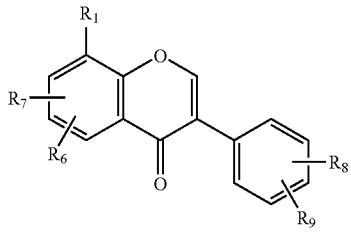
(IV)

or a protected derivative thereof wherein:
$R_1$, $R_6$, $R_7$, $R_8$ and $R_9$ are as defined above for compound of formula (II)

Access to compounds of general formula (IV) is available by general synthetic methods as set out in Scheme 1 below and as described in published International application No. WO01/17986, the disclosure of which is incorporated herein by reference. The general synthetic method is set out in Scheme 1.

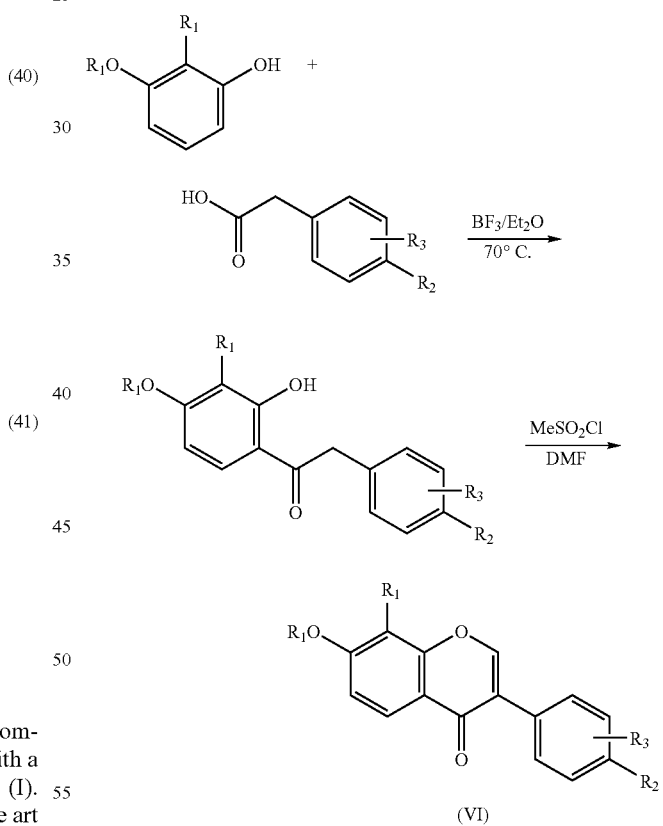

Compounds for use in the preferred synthetic methods of the present invention may be derived from any number of sources readily identifiable to a person skilled in the art. For example, daidzein is readily available or can be synthesised by standard methods known in the art. Suitable methods may be found in, for example, published International Patent Applications WO 98/08503 and WO 00/49009, and references cited therein, which are incorporated herein in their entirety by reference.

Clearly one or more of the above strategies may require the use of a one or more protecting groups in order to protect functionality in other parts of the molecule, when performing a particular treatment or step.

Preferably any free alcohols, esters or other such reactive groups will be protected, for example, as t-butyldimethylsilyl ethers during nucleophilic addition reactions.

Chemical modifications and manipulations may be performed on the compounds of the invention as would be known to one skilled in the art. For example, reaction of compound No. 1 with alkylating agents gives ether derivatives at the free phenolic groups. Halogenation of the aromatic rings is also possible and, for example, reaction with N-bromosuccinimide affords the 8-bromo derivative (compound 42) as the main component, with smaller amounts of the 6-bromo isomer. Further reactions can include demethylation of alkoxy groups by employing, for example, hydrogen bromide in acetic acid to afford the trihydroxy compound 43.

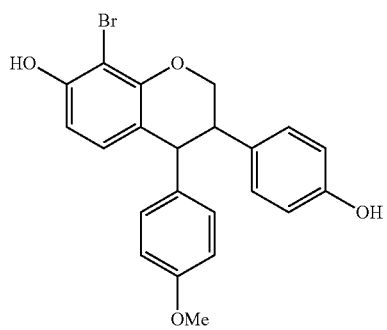
(42)

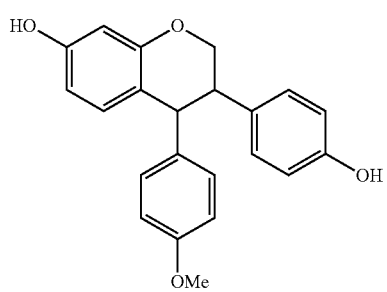
(43)

Additional compounds synthesised by the inventors include:

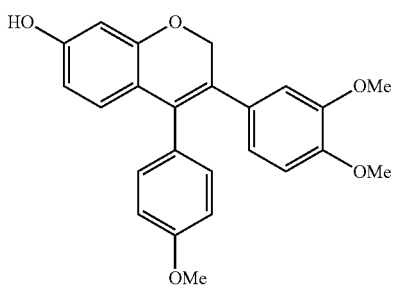
(44)

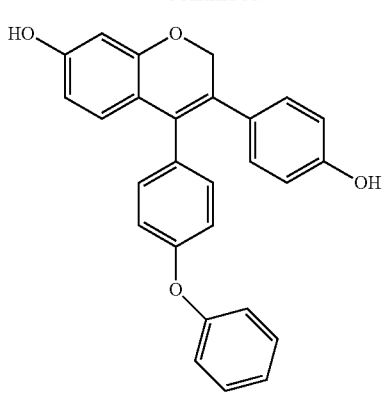
(45)

As used herein, the terms "treatment", "prophylaxis" or "prevention", "amelioration" and the like are to be considered in their broadest context. In particular, the term "treatment" does not necessarily imply that an animal is treated until total recovery. Accordingly, "treatment" includes amelioration of the symptoms or severity of a particular condition or preventing or otherwise reducing the risk of developing a particular condition.

The amount of one or more compounds according to the invention which is required in a therapeutic treatment will depend upon a number of factors, which include the specific application, the nature of the particular compound used, the condition being treated, the mode of administration and the condition of the patient.

Compounds of formula (I) may be administered in a manner and amount as is conventionally practised. See, for example, Goodman and Gilman, "The pharmacological basis of therapeutics", 7th Edition, (1985). The specific dosage utilised will depend upon the condition being treated, the state of the subject, the route of administration and other well known factors as indicated above. In general, a daily dose per patient may be in the range of 0.1 mg to 5 g; typically from 0.5 mg to 1 g; preferably from 50 mg to 200 mg. The length of dosing may range from a single dose given once every day or two, to twice or thrice daily doses given over the course of from a week to many months to many years as required, depending on the severity of the condition to be treated or alleviated.

It will be further understood that for any particular subject, specific dosage regimens should be adjust over time according to the individual need and the professional judgment of the person administering or supervising the administration of the compositions.

Relatively short-term treatments with the active compounds can be used to cause stabilisation or shrinkage or remission of cancers. Longer-term treatments can be employed to prevent the development of cancers in high-risk patients.

The production of pharmaceutical compositions for the treatment of the therapeutic indications herein described are typically prepared by admixture of the compounds of the invention (for convenience hereafter referred to as the "active compounds") with one or more pharmaceutically or veterinary acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain up to 100% by weight of the active compound, preferably from 0.5% to 59% by weight of the active compound.

The preferred concentration of active compound in the drug composition will depend on absorption, distribution, inactivation, and excretion rates of the drug as well as other factors known to those of skill in the art. One or more active compounds may be incorporated in the formulations of the invention.

The formulations of the invention include those suitable for oral, rectal, ocular, buccal (for example, sublingual), parenteral (for example, subcutaneous, intramuscular, intradermal, or intravenous), transdermal administration including mucosal administration via the nose, mouth, vagina or rectum, and as inhalants, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more other ingredients.

Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Formulations suitable for ocular administration include liquids, gels and creams comprising the active compound in an ocularly acceptable carrier or diluent.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and can be administered at a rate of 0.1 ml/minute/kg.

Formulations suitable for rectal administration are preferably presented as unit dose suppositories. Formulations suitable for vaginal administration are preferably presented as unit dose pessaries. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vaseline, lanoline, polyethylene glycols, alcohols, and combination of two or more thereof. The active compound is generally present at a concentration of from 0.1% to 5% w/w, more particularly from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound. See for example Brown, L., et al. (1998).

Formulations suitable for transdermal administration may also be delivered by iontophoresis (see, for example, Panchagnula R, et al., 2000) and typically take the form of an optionally buffered aqueous solution of the active compound. Suitable formulations comprise citrate or Bis/Tris buffer (pH 6) or ethanol/water and contain from 0.1 M to 0.2 M active ingredient.

Formulations suitable for inhalation may be delivered as a spray composition in the form of a solution, suspension or emulsion. The inhalation spray composition may further comprise a pharmaceutically acceptable propellant such as a hydrogen containing fluorocarbon such as 1,1,1,2-tetrafluoroethane or 1,1,1,2,3,3,3-heptafluoro-n-propane.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

In a preferred aspect the invention provides a method of treating humans by administering an effective amount of one or more compounds according to the invention or a composition containing the same.

The active compound or pharmaceutically acceptable derivatives prodrugs or salts thereof can also be co-administered with other active materials that do not impair the desired action, or with materials that supplement the desired action, such as antibiotics, antifungals, antiinflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; antithrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal antiinflammatories such as ibuprofen, indomethacin, aspirin, fenoprofen, mefenamic acid, flufenamic acid and sulindac or an antiemetic such as zofran®. The compounds can also be administered with corticosteroids.

Compounds of formula (I) seem to be particularly suitable for co-administration with other anti-cancer drugs such as cisplatin and/or dehydroequol and/or paclitaxel (Taxol®). This may result in improved effects in the treatment in comparison to when only one of the medicaments is employed.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second or later active agent is administered, especially where a cumulative or synergistic effect is desired.

The invention also extends to novel intermediates employed in the preparation of compounds according to the invention.

The compounds of the invention are useful in the treatment, prevention or amelioration of diseases associated with aberrant cell survival, aberrant cell proliferation, abnormal cellular migration, abnormal angiogenesis, abnormal estrogen/androgen balance, dysfunctional or abnormal steroid genesis, degeneration including degenerative changes within blood vessel walls, inflammation, and immunological imbalance.

The invention is further illustrated by the following non-limiting Examples and accompanying drawings.

EXAMPLES

Example 1

3-(4-hydroxyphenyl)-4-(4-methoxyphenyl)-8-methyl-3,4-dihydro-2H-chromen-7-ol

Step 1 1-(2,4-Dihydroxy-3-methyl-phenyl)-2-(4-hydroxy-phenyl)-ethanone

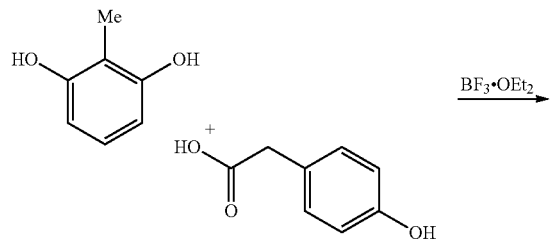

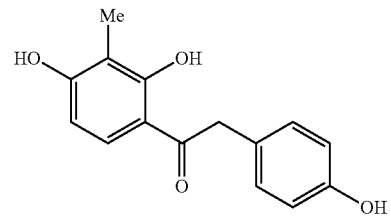

2-Methylresorcinol (4.00 g, 1 equivalent) and 4-Hydroxyphenylacetic acid (5.00 g, 1 equivalent) were added to a round bottom flask. The round bottom flask was attached to a condenser and placed in an oil bath, the whole system was kept under nitrogen. Distilled $BF_3 \cdot OEt_2$ (20 ml, 5 equiv.) was added to the mixture while stirring. The mixture was refluxed (110° C.). A yellow solid formed at 20 minutes indicating that the reaction had gone to completion. The reaction was left on heat for a further 10 minutes and then cooled to room temperature. The yellow solid was collected by suction filtration and washed with distilled water (200 ml) to remove any excess $BF_3 \cdot OEt_2$ present. $^1H$ NMR in d-DMSO indicated the yellow solid was 1-(2,4-Dihydroxy-3-methyl-phenyl)-2-(4-hydroxy-phenyl)-ethanone in >95% purity. The solid was dried on a freeze dryer for 24 hours (8.93 g, 99%).

Step 2 7-Hydroxy-3-(4-hydroxy-phenyl)-8-methyl-chromen-4-one

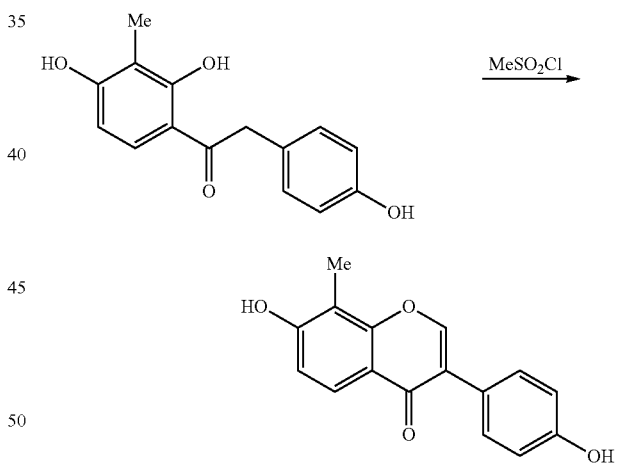

1-(2,4-Dihydroxy-3-methyl-phenyl)-2-(4-hydroxy-phenyl)-ethanone (3.99 g) and N,N-DMF (115 ml) were added to a 500 ml 2-neck round bottom flask, the flask was attached to a condenser and placed in an oil bath. A dropping funnel was attached to the round bottom flask, and the whole system was kept under nitrogen. The flask was heated and maintained at 50° C. $BF_3 \cdot OEt_2$ (57 ml, 29 equiv.) was added drop wise to the solution over a period of 15 minutes, producing fumes. Methane sulfonyl chloride (MeSO$_2$Cl) (14 ml, 12 equiv.) was added to N,N-DMF (14 ml) in the dropping funnel. This mixture was then added drop wise to the round bottom flask over a period of 10 minutes. Once addition was complete, the temperature was increased to reflux (110° C.). The reaction was monitored by HPLC (NV06_R&D.m) and was completed at 1 hr and 44 mins. The mixture was cooled to room temperature and poured into chilled stirred distilled water (4 L). A bright yellow floccular precipitate was immediately produced and the mixture was left stirring in the cold room overnight. The mixture was then filtered through a buchner funnel, to give a yellow solid. ¹HNMR of the solid in d-DMSO indicated it was 7-Hydroxy-3-(4-hydroxy-phenyl)-8-methyl-chromen-4-one with >95% purity. The solid was dried on a freeze dryer for 24 hours. When dry, the solid was weighed (2.73 g, 66%).

Step 3 Acetic acid 3-(4-hydroxy-phenyl)-8-methyl-4-oxo-4H-chromen-7-yl ester

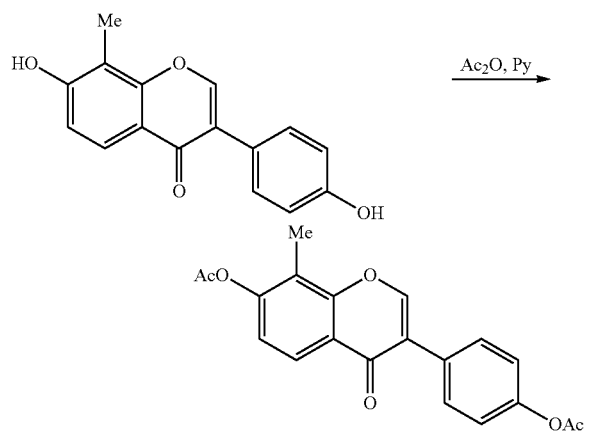

Hydroxy-3-(4-hydroxy-phenyl)-8-methyl-chromen-4-one (35.18 g) were combined into a round bottom flask (1 L). Pyridine (38 ml, 2 equivalents) and acetic anhydride (576 ml, 47 equivalents) were added to the round bottom flask while stirring at room temperature. The reaction was monitored by HPLC and was completed instantaneously. There was a change in colour observed, the reaction mixture was dark brown initially and went bright orange with tan brown floccular particles upon stirring. The reaction mixture was poured into chilled, distilled H₂O (4 L) and was left stirring at room temperature for 30 minutes. An off-white solid was collected by suction filtration. ¹HNMR of the solid in d-CDCl₃ indicated it was Acetic acid 3-(4-hydroxy-phenyl)-8-methyl-4-oxo-4H-chromen-7-yl ester with >95% purity The solid was dried on a freeze dryer for 24 hours. When dry, the solid was weighed (31.80 g, 69%).

Step 4 Acetic acid 3-(4-hydroxy-phenyl)-8-methyl-4-oxo-chroman-7-yl ester

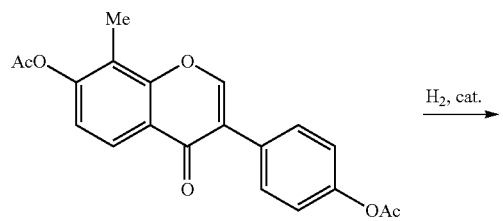

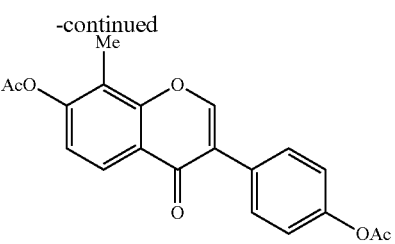

Acetic acid 3-(4-hydroxy-phenyl)-8-methyl-4-oxo-4H-chromen-7-yl ester (26.32 g), 10% Pd/Al₂O₃ (12.93 g, 50%) and ethyl acetate (EtOAc) (1.5 L) were added to a hydrogenation round bottom flask (2 L). The flask was placed on the hydrogenator, evacuated, purged with nitrogen gas (×5) and hydrogen gas (×5). The reaction was monitored by HPLC. 10% Pd/Al₂O₃ (9 g, 35%) was added to the round bottom flask at 40 hours, indicated there was no product peak present, only starting material was present. HPLC at 62 hours indicated that the major peak was product peak with starting material peak being half height of product peak. 10% Pd/Al₂O₃ (5.69 g, 20%) was added to the round bottom flask to speed up reaction rate. Reaction was completed at 64 hours. The reaction mixture was filtered through celite to remove the Pd/Al₂O₃ catalyst, the celite was rinsed with EtOAc (1 L) to ensure majority of product was collected. The EtOAc was evaporated off on a rotary evaporator to give a yellow solid. The solid was re-crystallised in 95% EtOH (650 ml) and left in the freezer overnight. Off-white crystals were collected by suction filtration. ¹HNMR in d-CDCl₃ indicated the off-white crystals were 8Acetic acid 3-(4-hydroxy-phenyl)-8-methyl-4-oxo-chroman-7-yl ester with >95% purity. The crystals were stored in a desiccator for 24 hours, and weighed (18.37 g, 69%).

Step 5 7-Hydroxy-3-(4-hydroxy-phenyl)-8-methyl-chroman-4-one

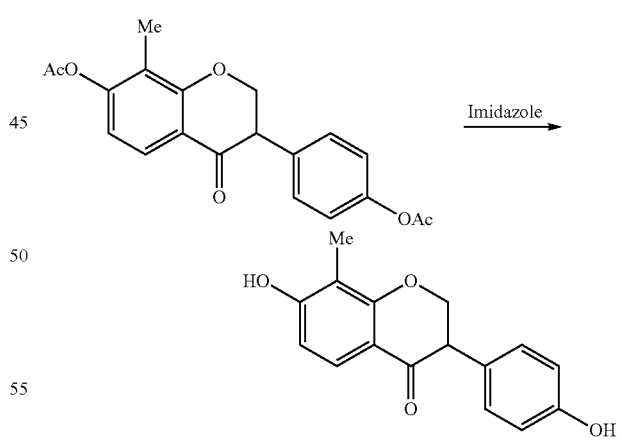

Acetic acid 3-(4-hydroxy-phenyl)-8-methyl-4-oxo-chroman-7-yl ester (18.37 g), imidazole (21.18 g, 6 equivalents) and 100% EtOH (536 ml) were added to a round bottom flask (2 L). The reaction mixture was refluxed and monitored by HPLC. The reaction was completed at 8 hours. The reaction mixture was reduced (~130 ml) on a rotary evaporator and poured into stirred, chilled distilled water (1.9 L). The water crash out was left stirring in the cold room overnight. The pale pink solid was collected by suction filtration. ¹H NMR of the solid indicated it was 7-Hydroxy-3-(4-hydroxy-phenyl)-8-methyl-chroman-4-one with >95% purity. The solid was dried on the freeze dryer for 3 hours (8.31 g, 59%).

Step 6 7,4'-Bis tert-butyldimethylsilyloxy-8-methyl-dihydrodaidzein

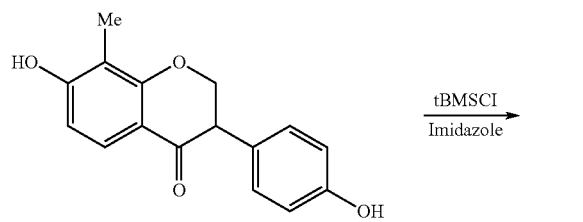

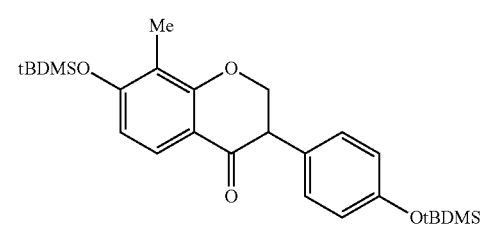

8-methyldihydrodaidzein 4.2 g, imidazole 13 g, tert-butyldimethylsilyl chloride 12.7 g (70 mmoles), and N,N-DMF 50 ml were combined in a 250 mlL round bottom flask and stirred under nitrogen at room temperature for 16 hours. The reaction was quenched with the addition of chilled water (100 ml) with the reaction mix cooled in an ice bath. A white solid was filtered off, rinsed with water. Recrystallisation from ethanol afforded white fluffy crystals 3.2 g.

Step 7 7-(tert-butyldimethylsilyloxy)-3-3-(4-(tert-butyldimethylsilyloxy) phenyl-4-(4-methoxypenyl)-8-methyl-3,4-dihydro-2H-chromen-4-ol

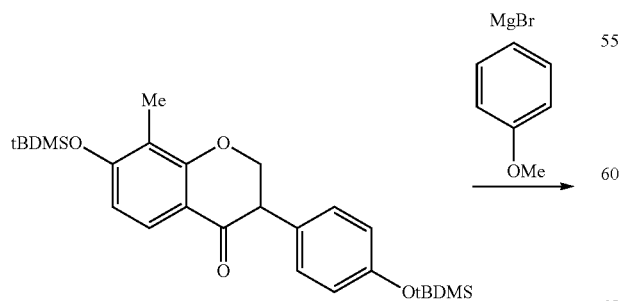

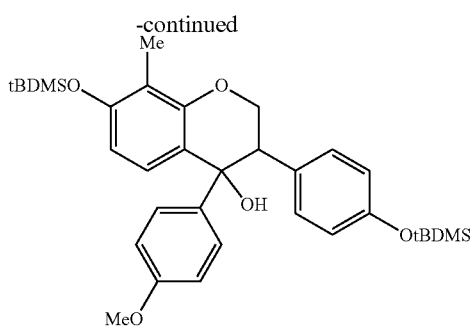

2.5 g of the product of step 6 was weighed in a 2-neck round bottom flask, and flushed under nitrogen. Anhydrous THF 10 ml was added to the reaction vessel to give a clear slightly yellow solution. A condenser was attached and the reaction vessel placed in an ice bath. Commercial 4-methoxyphenyl-magnesium bromide (0.5M solution in THF) 22.5 ml was added to the reaction mix dropwise over 10 minutes. The reaction was quenched by the dropwise with wet ether (50:50 $H_2O$: diethyl ether) while still under nitrogen, with a white precipitate forming as increasing amounts of $H_2O$ added. A further amount of water was added to the reaction mix before extraction with diethyl ether.

The organic layers were combined and washed with water, brine, dried over anhydrous magnesium sulphate and solvent removed in vacuo to give clear yellow oil which solidified overnight to give an off-white solid. The oily nature of the material precluded an accurate yield being calculated. There was no further clean up of the product before use in the next reaction. The oily nature of the material precluded an accurate yield being calculated.

Step 8 3-(4-hydroxyphenyl)-4-(4-methoxyphenyl)-2H-chromen-7-ol

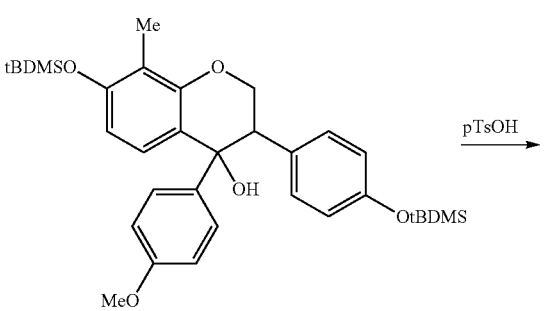

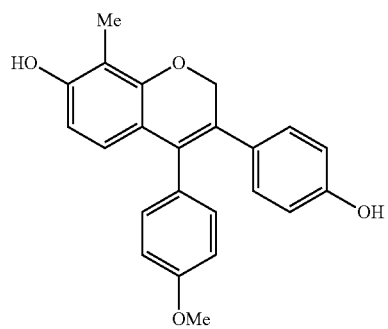

4.2 g of the product of step 7, pTsOH (para-toluene sulphoric acid) 4.5 g boiling chips and 200 ml of ethanol were combined in a 2-neck 500 ml round bottom flask with condenser attached. The reaction was heated at reflux for 3 hours. The solvent was concentrated in vacuo to ~20 ml before being poured into chilled, stirred water (100 ml). The mixture was then extracted with ethyl acetate, the combined organic layers washed with water (3×100 ml), brine (1×100 ml), dried over anhydrous magnesium sulphate and filtered and solvent removed in vacuo to give red/brown oil. The oil was dissolved in methanol (~15 ml) and put in freezer overnight.

A white precipitate had formed overnight which was filtered off and rinsed with methanol. The filtrate was concentrated in vacuo to give a brown oil.

Step 9 3-(4-hydroxyphenyl)-4-(4-methoxyphenyl)-8-methyl-3,4-dihydro-2H-chromen-7-ol

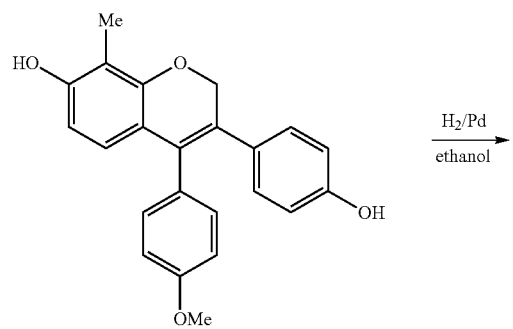

2.5 g of the product of step 8, 10% Pd/Al$_2$O$_3$ 0.4 g and 50 ml of ethanol were combined in a 2-neck 100 ml round bottom flask. The reaction was hydrogenated at low pressure using standard conditions for 3 hours. The reaction was filtered through Celite to remove the catalyst, rinsed through with ethanol (100 ml). The filtrate was concentrated to ~15 ml before being poured into chilled, stirred water (300 mL). A pale orange precipitate formed which then formed a brown oil. The mixture was then extracted with diethyl ether, the combined organic layers washed with water (3×100 ml), brine (1×100 ml), dried over anhydrous magnesium sulphate and filtered. The solvent was removed in vacuo to give red/brown oil. The product was recrystallised from diethyl ether (~15 ml), to give brown solid which was rinsed with chilled diethyl ether to give off-white crystals. 4 crops of (IV), ~1 g. The $^1$H NMR spectrum and numbering scheme being shown below.

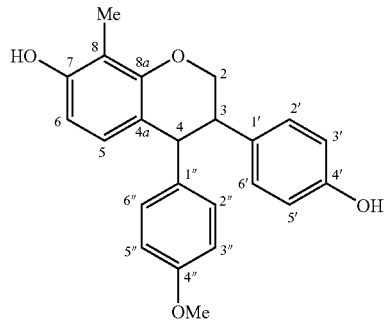

| H | δppm | Peak Shape | J Hz | Integrates | Comments |
|---|---|---|---|---|---|
| C2equatorial | 4.13 | m | | 1 | |
| C2axial | 4.25 | m | | 1 | |
| C3 | 3.31 | m | | 1 | Partially obscured by water paek |
| C4 | 4.28 | m | | 1 | |
| C5 | 6.44 | d | 8.050 | 1 | |
| C6 | 6.30 | d | 8.4 | 1 | |
| C8-Me | 2.0 | s | — | 3 | |
| C2', C6' | 7.5 | d | 8.7 | 2 | |
| C3', C5' | 6.92 | d | 8.7 | 2 | |
| C2", C6" | 6.60 | d | 8.7 | 2 | |
| C3", C5" | 6.43 | d | 8.7 | 2 | |
| OMe | 3.8 | s | 0 | 3 | |

Example 2

3-(4-hydroxyphenyl)-4-(4-methoxyphenyl)-3',4'-dimethoxy-8-methyl-3,4-dihydro-2H-chromen-7-ol

Step 1.1 1-(2,4-dihydroxy-3-methyl-phenyl)-2-(3,4-dimethoxy-phenyl) ethanone

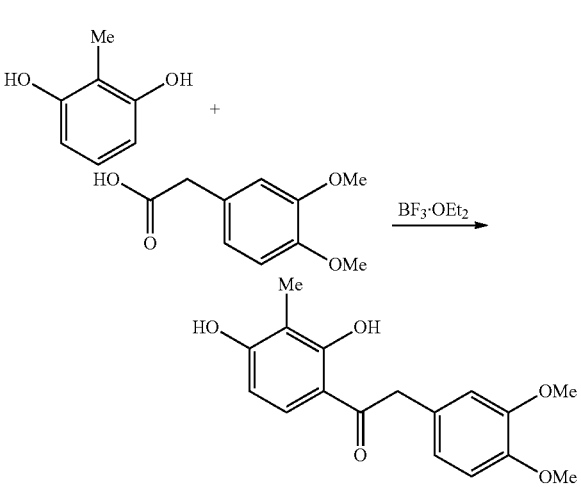

2-Methylresorcinol (6.285 g, 1 equivalent) and 3,4-dimethoxyphenylacetic acid (9.251 g, 1 equivalent) were added to a round bottom flask. The round bottom flask was attached to a condenser and placed in an oil bath, the whole system was kept under nitrogen. Distilled boron trifluoride diethyl etherate, BF$_3$.OEt$_2$ (42 ml, 5 equiv.) was added to the mixture while stirring. The mixture was refluxed (110° C.). A yellow solid formed at 75 minutes indicating that the reaction had gone to completion. The reaction was heated for a further 10 minutes and cooled to room temperature. The yellow solid was collected by suction filtration and washed with distilled water (200 ml) to remove any excess $BF_3.OEt_2$ present. $^1H$ NMR in d-DMSO indicated the yellow solid was 1-(2,4-dihydroxy-3-methyl-phenyl)-2-(3,4-dimethoxy-phenyl) ethanone in >95% purity. The solid was dried on a freeze dryer for 24 hours (6.303 g, 43%).

Step 2.1 3-(3,4-dimethoxy-phenyl)-7-hydroxy-8-methyl-chromen-4-one

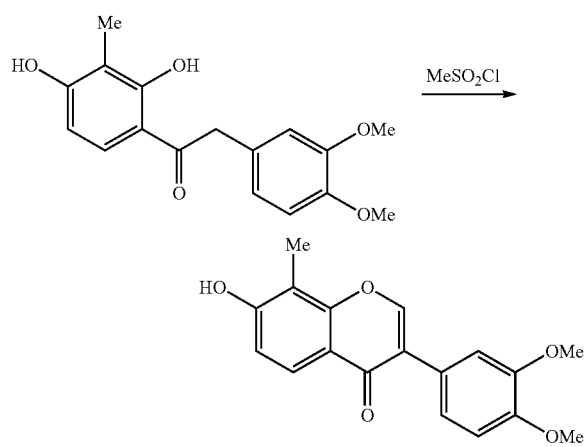

1-(2,4-dihydroxy-3-methyl-phenyl)-2-(3,4-dimethoxy-phenyl) ethanone (1078-1-49; 9.999 g, 34.4 mmol) was dissolved in N,N-DMF (15 mL), dried with $MgSO_4$. Under an $N_2$ atmosphere, distilled $BF_3$-$OEt_2$ (16.08.04) was added dropwise at r.t. Heat begun after 20 min. After 1 h, methane sulfonyl chloride in DMF (8 mL in 20 mL) was slowly added at 50° C. The reaction mixture was heated to reflux for 1.5 h. The dull yellow solution was added to 1.2 L of cold, vigorously stirred water which was left at 4° C. overnight. The dull yellow solid was collected by filtration, then placed in water to remove residual $BF_3$-$OEt_2$. Solid was collected by filtration and dried using a freeze-dryer overnight. $^1H$ NMR in d-DMSO indicated the yellow solid was 3-(3,4-dimethoxy-phenyl)-7-hydroxy-8-methyl-chromen-4-one in 90% purity (8.85 g, 82%).

Step 3.1 acetic acid 3-(3,4-dimethoxy-phenyl)-8-methyl-4-oxo-4H-chromen-7-yl ester

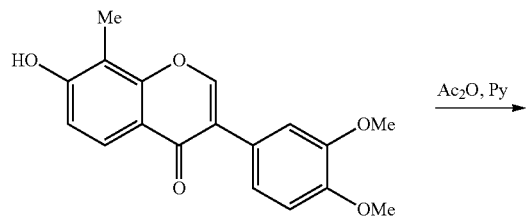

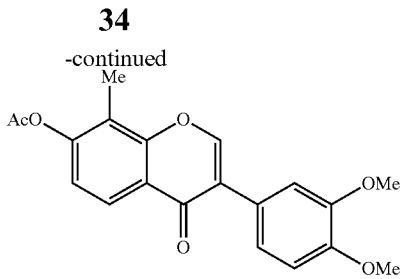

3-(3,4-dimethoxy-phenyl)-7-hydroxy-8-methyl-chromen-4-one (9.82 g, 31 mmol), acetic anhydride (62 ml) and pyridine (6.2 ml) were combined in a round bottom flask and heated to reflux. The reaction was cooled to room temperature after 3 hours of heating, and a crystalline solid formed. The solid was filtered and rinsed with $H_2O$ (1 L). $^1H$ NMR in d-$CDCl_3$ indicated pale brown crystals was acetic acid 3-(3,4-dimethoxy-phenyl) -8-methyl-4-oxo-4H-chromen-7-yl ester in 90% purity (7.214 g, 71%).

Step 4.1 Acetic acid 3-(3,4-dimethoxy-phenyl)-8-methyl-4-oxo-chroman-7-yl ester

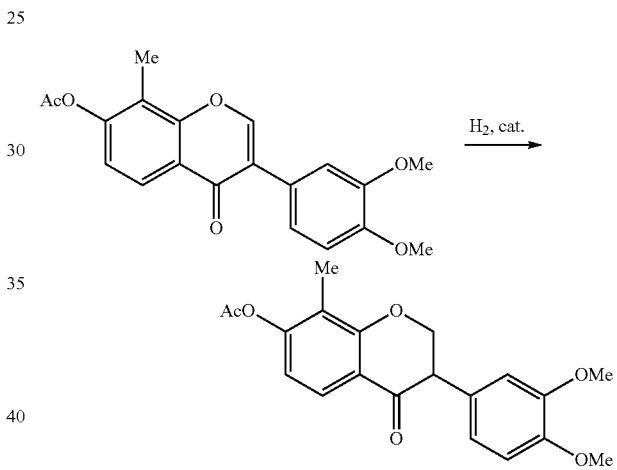

3-(3,4-dimethoxy-phenyl)-8-methyl-4-oxo-4H-chromen-7-yl ester (1.12 g, 3 mmol), 10% Pd/$Al_2O_3$ (0.501 g, 45% w/w) and dry EtOAc (100 ml) were placed in a 2-neck round bottom flask and placed on the hydrogenator. After 4 hours, 1 major product was observed. The reaction was purged and the catalyst filtered off through celite. The filtrate was reduced to give a white solid. $^1H$ NMR in d-$CDCl_3$ indicated the solid was Acetic acid 3-(3,4-dimethoxy-phenyl)-8-methyl-4-oxo-chroman-7-yl ester in 85% purity (1.1 g).

Step 5.1 3-(3,4-Dimethoxy-phenyl)-7-hydroxy-8-methyl-chroman-4-one

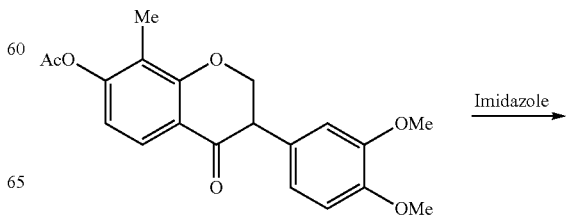

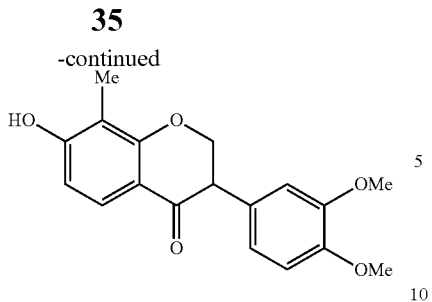

Acetic acid 3-(3,4-dimethoxy-phenyl)-8-methyl-4-oxo-chroman-7-yl ester (1.1 g, 3.2 mmol) and imidazole (3.2 g, 47 mmol) were refluxed in EtOH (100 ml). The reaction was complete after 90 minutes and allowed to cool to room temperature before pouring into stirred H$_2$O (800 ml). A fine white precipitate was filtered off and $^1$H NMR in d-CDCl$_3$ indicated the solid was 3-(3,4-Dimethoxy-phenyl)-7-hydroxy-8-methyl-chroman-4-one in >95% purity (0.31 g, 30%).

Step 6.1 7,4'-Bis tert-butyldimethylsilyloxy-3',4'-dimethoxy-8-methyl-dihydrodaidzein

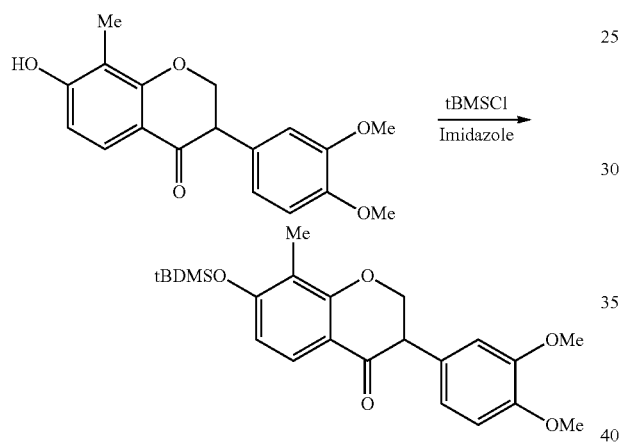

3',4'Dimethoxy-8-methyldihydrodaidzein 2 g, imidazole 6.8 g, tert Butyldimethylsilyl chloride 6.3 g, and N,N-DMF 50 ml were combined in a 250 mlL round bottom flask and stirred under nitrogen at room temperature for 16 hours. The reaction was quenched with the addition of chilled water (100 ml) with the reaction mix cooled in an ice bath. A white solid was filtered off, rinsed with water. Recrystallisation from ethanol afforded white fluffy crystals 2.2 g

Step 7.1 7-(tert-butyldimethylsilyloxy)-3-3-(4-(tert-butyldimethylsilyloxy)phenyl)-4-(4-methoxypenyl)-3',4'dimethoxy-8-methyl-3,4-dihydro-2H-chromen-4-ol

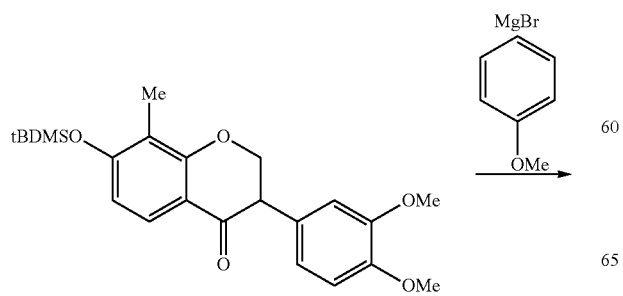

The product of step 6.1 above 2 g was weighed in a 2-neck round bottom flask, and flushed under nitrogen. Anhydrous THF 10 ml was added to the reaction vessel to give a clear slightly yellow solution. A condenser was attached and the reaction vessel placed in an ice bath. Commercial 4-methoxyphenylmagnesium bromide (0.5M solution in THF) 22.5 ml was added to the reaction mix dropwise over 10 minutes. The reaction was quenched by the dropwise with wet ether (50:50 H$_2$O: diethyl ether) while still under nitrogen, with a white precipitate forming as increasing amounts of H$_2$O added. A further amount of water was added to the reaction mix before extraction with diethyl ether. The organic layers were combined and washed with water, brine, dried over anhydrous magnesium sulphate and solvent removed in vacuo to give clear yellow oil which solidified overnight to give an off-white solid. The oily nature of the material precluded an accurate yield being calculated. There was no further clean up of the product before use in the next reaction. The oily nature of the material precluded an accurate yield being calculated.

Step 8.1 3-(4-hydroxyphenyl)-4-(4-methoxyphenyl)-3',4'-dimethoxy-8-methyl-2H-chromen-7-ol

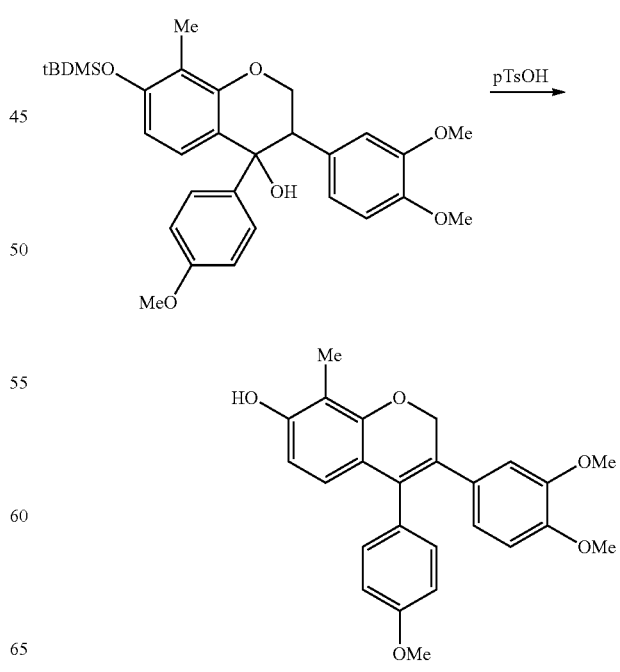

2 g of the product of step 7.1 pTsOH 4.5 g boiling chips and 100 ml of ethanol were combined in a 2-neck 500 ml round bottom flask with condenser attached. The reaction was heated at reflux for 3 hours. The solvent was concentrated in vacuo to ~10 ml before being poured into chilled, stirred water (100 ml). The mixture was then extracted with ethyl acetate, the combined organic layers washed with water (3×100 ml), brine (1×100 ml), dried over anhydrous magnesium sulphate and filtered and solvent removed in vacuo to give red/brown oil. The oil was dissolved in methanol (~15 ml) and put in freezer overnight.

A white precipitate had formed overnight which was filtered off and rinsed with methanol. The filtrate was concentrated in vacuo to give a brown oil, which was crashed out into water to give a pale brown solid.

Step 9.1 3-(4-hydroxyphenyl)-4-(4-methoxyphenyl)-3',4'-dimethoxy-8-methyl-3,4-dihydro-2H-chromen-7-ol

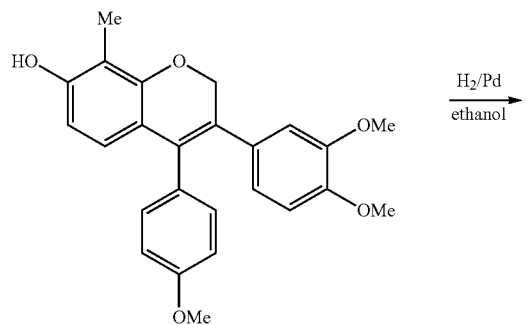

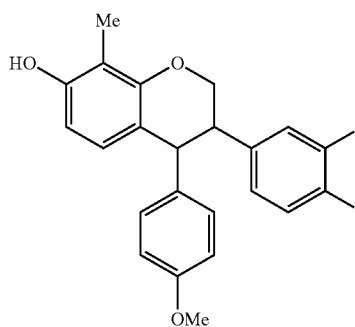

1 g of the product of step 8.1 10% Pd/Al$_2$O$_3$ 0.2 g and 25 ml of ethanol were combined in a 2-neck 100 ml round bottom flask. The reaction was hydrogenated at low pressure using standard conditions for 3 hours. The reaction was filtered through Celite to remove the catalyst, rinsed through with ethanol (100 ml). The filtrate was concentrated to ~5 ml before being poured into chilled, stirred water (100 mL). A pale orange precipitate formed which then formed a brown oil. The mixture was then extracted with diethyl ether, the combined organic layers washed with water (3×100 ml), brine (1×100 ml), dried over anhydrous magnesium sulphate and filtered. The solvent was removed in vacuo to give red/brown oil. The product was recrystallised from diethyl ether (~5 ml), to give brown solid which was rinsed with chilled diethyl ether to give off-white crystals. 4 crops of (IV), ~0.2 g. The $^1$H NMR spectrum and numbering scheme shown below.

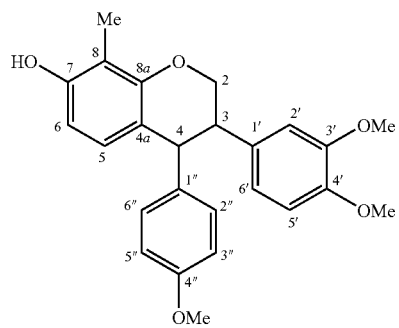

| H | Chemical shift | Peak Shape | J Hz | Integrates | Comments |
|---|---|---|---|---|---|
| C2equatorial | 4.05 | m | | 1 | |
| C2axial | 4.25 | m | | 1 | |
| C3 | 3.38 | m | | 1 | Partially obscured by water peak |
| C4 | 4.45 | m | | 1 | |
| C5 | 6.80 | d | 8.4 | 1 | |
| C6 | 6.38 | d | 8.4 | 1 | |
| C8-Me | 2.1 | s | — | 3 | |
| C2' | 7.1 | d | 2.1 | 1 | |
| C5' | 6.95 | d | 8.4 | 1 | |
| C6' | 6.98 | dd | 2.1, 8.4 | 1 | |
| C2", C6" | 6.66 | d | 8.7 | 2 | |
| C3", C5" | 6.33 | d | 8.7 | 2 | |
| OMe x3 | 3.8, 3.82, 3.83 | s | 0 | 9 | |

$^1$H N.m.r. assignments are provided for the following compounds:

Cpd. 14

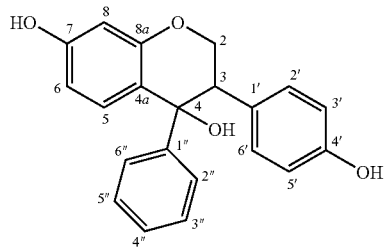

| H | δ ppm | Peak Shape | J Hz | Integrates | Comments |
|---|---|---|---|---|---|
| C2 | 3.30 | dd | 3.293, 11.709 | 1 | dd is slightly under H$_2$O peak |
| C2 | 4.05 | dd | 3.659, 10.612 | 1 | |
| C3 | 4.62 | dd | 10.612, 12.075 | 1 | dd is overlapped |
| C5 | 6.45 | d | | | Under C3', C5' doublet |
| C6 | 6.20 | dd | 2.561, 8.416 | 1 | |
| C8 | 6.23 | d | 2.196 | 1 | Adjacent to O |
| C2', C6' | 6.70 | d | 8.782 | 2 | |
| C3', C5' | 6.45 | d | 8.782 | 2 | Integrates for 3 in total including C5 |
| C2", C6" | 7.11 | m | | 2 | Overlapping with 4", 3", 5", cannot measure J |
| C3", C5" | 7.11 | m | | 2 | Overlapping with 4", 2", 6" cannot measure J |
| C4" | 7.11 | m | | 1 | Overlapping with 3", 5", 4" cannot measure J |

Cpd. 30

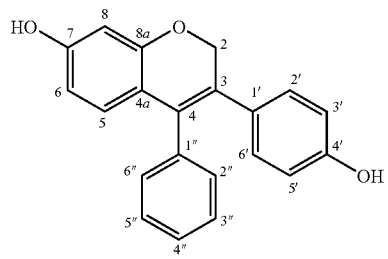

| H | δ ppm | Peak Shape | J Hz | Integrates | C | Comments |
|---|---|---|---|---|---|---|
| C2 | 4.95 | s | | 2 | 69 | |
| C3 | — | | | | | |
| C4 | — | | | | | |
| C4a | — | | | | 116.5 | |
| C5 | 6.43 | d | 8.416 | 1 | 130.5 | |
| C6 | 6.30 | dd | 2.561, 8.416 | 1 | 108 | |
| C7 | | | | | 156 | |
| C8 | 6.30 | d | 2.561 | 1 | 102 | Adjacent to O |
| C8a | | | | | 158 | |
| C1' | | | | | | |
| C2', C6' | 6.79 | d | 8.416 | 2 | 128 | |
| C3', C5' | 6.49 | d | 8.416 | 2 | 114.5 | |
| C4' | | | | | 155 | Adjacent to O |
| C1" | | | | | | |
| C2", C6" | 7.04 | m | | 2 | 130 | |
| C3", C5" | 7.27 | m | | 2 | 129 | Overlapping with 4", cannot measure J |
| C4" | 7.27 | m | | 1 | 126.5 | Overlapping with 3", 5", cannot measure J |

Cpd. 12
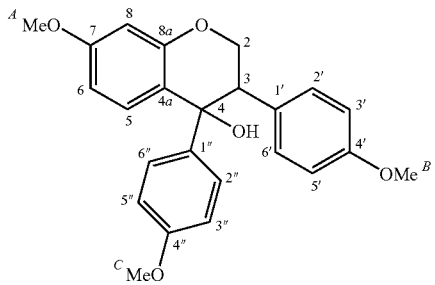
| H | δ ppm | Peak Shape | J Hz | Integrates | Comments |
|---|---|---|---|---|---|
| C2equatorial | 4.30 | dd | 3.659, 10.612 | 1 | |
| C2axial | 4.69 | dd | 10.978 | 1 | dd is overlapped |
| C3 | 3.44 | dd | 3.293, 10.978 | 1 | |
| C5 | 6.83 | d | 8.782 | 1 | |
| C6 | 6.43 | dd | 2.561, 8.416 | 1 | |
| C8 | 6.47 | d | 2.561 | 1 | |
| C2', C6' | 6.83 | d | 8.782 | 2 | |
| C3', C5' | 6.71 | d | 8.782 | 2 | |
| C2", C6" | 7.05 | d | 8.782 | 2 | |
| C3", C5" | 6.76 | d | 8.782 | 2 | |
| Me A | 3.75 | s | — | 3 | Methoxy peaks are interchangeable |
| Me B | 3.79 | s | — | 3 | |
| Me C | 3.79 | s | — | 3 | |
Cpd. 28
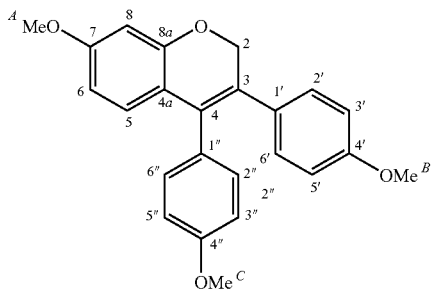
| H | δ ppm | Peak Shape | J Hz | Integrates | Comments |
|---|---|---|---|---|---|
| C2 | 5.05 | s | — | 2 | |
| C5 | 6.75 | d | 8.416 | 1 | |
| C6 | 6.38 | dd | 2.561, 8.416 | 1 | |
| C8 | 6.50 | d | 2.651 | 1 | |
| C2', C6' | 6.90 | d | 8.782 | 2 | |
| C3', C5' | 6.67 | d | 8.782 | 2 | |
| C2", C6" | 7.02 | d | 8.782 | 2 | |
| C3", C5" | 6.81 | d | 8.416 | 2 | |
| Me A | 3.74 | s | — | 3 | Methoxy peaks are interchangeable |
| Me B | 3.79 | s | — | 3 | |
| Me C | 3.81 | s | — | 3 | |

Cpd. 31

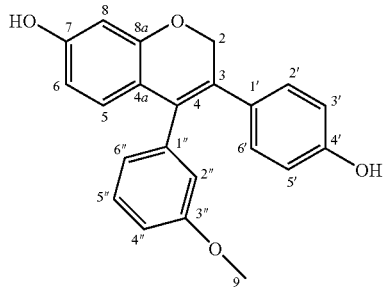

| H | δ ppm | Peak Shape | J Hz | Integrates | Comments |
|---|---|---|---|---|---|
| C2 | 4.93 | s | | 2 | |
| C5 | 6.28 | d | 2.196 | 1 | |
| C6 | 6.24 | dd | 2.196, 8.416 | 1 | |
| C8 | 6.47 | d | 8.416 | 1 | |
| C9 | 3.63 | s | | 3 | |
| C2', C6' | 6.82 | d | 8.416 | 2 | Overlapping with C2', C6' |
| C3', C5' | 6.51 | d | 8.416 | 2 | |
| C2" | 6.57 | | | 1 | |
| C4" | 6.81 | | | 1 | |
| C5" | 7.20 | t | 8.050 | 1 | |
| C6" | 6.63 | | | 1 | |

Cpd. 10

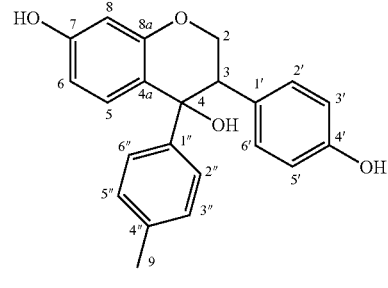

| H | δ ppm | Peak Shape | J Hz | Integrates | Comments |
|---|---|---|---|---|---|
| C2 | 3.30 | dd | | 1 | under H$_2$O peak |
| C2 | 4.02 | dd | 4.391, 11.343 | 1 | |
| C3 | 4.60 | dd | 10.612, 12.075 | 1 | dd is overlapped |
| C5 | 6.21 | d | 2.196 | 1 | |
| C6 | 6.18 | dd | 2.561, 8.416 | 1 | |
| C8 | 6.42 | d | 8.416 | 1 | Overlapping with C3', C5' |
| C9 | 2.21 | s | | 3 | |
| C2', C6' | 6.72 | d | 8.782 | 2 | |
| C3', C5' | 6.44 | d | 8.416 | 2 | Overlapping with C8 |
| C2", C6" | 6.94 | d | 8.050 | 2 | |
| C3", C5" | 7.01 | d | 8.050 | 2 | |

Cpd. 11

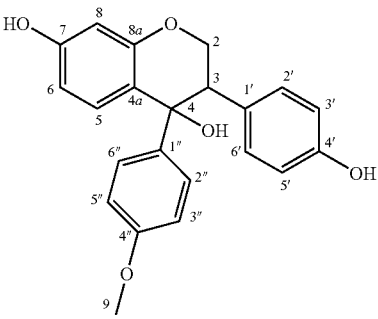

| H | δ ppm | Peak Shape | J Hz | Integrates | Comments |
|---|---|---|---|---|---|
| C2 | 3.30 | dd | 3.659, 11.709 | 1 | dd is slightly under H$_2$O peak, measured J from previous NMR |
| C2 | 4.05 | dd | 3.659, 10.612 | 1 | |
| C3 | 4.62 | dd | 10.978, 11.709 | 1 | dd is overlapped |
| C5 | 6.47 | d | 8.416 | 1 | Overlapping with C3', C5' doublet |
| C6 | 6.20 | dd | 2.561, 8.416 | 1 | Overlapping with C8 doublet |
| C8 | 6.23 | d | 2.196 | 1 | Overlapping with C6 dd |
| C9 | 3.65 | s | | 3 | |
| C2', C6' | 6.72 | d | 8.416 | 2 | |
| C3', C5' | 6.45 | d | 8.416 | 2 | Integrates for 3 in total including C5 |
| C2", C6" | 6.70 | d | 8.782 | 2 | |
| C3", C5" | 7.03 | d | 8.782 | 2 | |

Cpd. 27

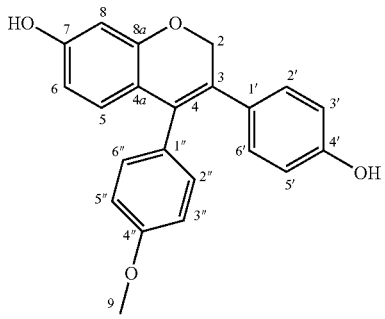

| H | δ ppm | Peak Shape | J Hz | Integrates | Comments |
|---|---|---|---|---|---|
| C2 | 4.94 | s | | 2 | |
| C5 | 6.48 | d | 8.416 | 1 | |
| C6 | 6.25 | dd | 2.561, 8.416 | 1 | |
| C8 | 6.30 | d | 2.561 | 1 | |
| C9 | 3.65 | s | | 3 | |
| C2', C6' | 6.81 | d | 8.416 | 2 | C2', C3', C2", C3" based on |
| C3', C5' | 6.53 | d | 8.782 | 2 | previous $^1$H NMR |
| C2", C6" | 6.86 | d | 8.782 | 2 | assignment for similar |
| C3", C5" | 6.97 | d | 8.782 | 2 | compounds. this assignment. |

2.0. Materials and Methods
2.1. Tissue Culture

The human pancreatic cancer cell line, HPAC (CRL-2119) was routinely cultured in 1:1 mixture DMEM (Sigma) plus Ham's F12 (Sigma) medium containing HEPES (15 mM), insulin (0.002 mg/ml), transferrin (0.005 mg/ml), hydrocortisone, (40 ng/ml), epidermal growth factor (10 ng/ml). The ovarian cancer cell lines; CP70 was obtained as a gift from Dr. Gil Mor (Yale University) and cultured in a 1:1 mixture DMEM plus Ham's F12 medium, and SKOV-3 was purchased from ATCC and cultured in McCoys 5a medium. The breast cancer cell line MDA-MB-468 were cultured in Leibovitz's L-15 medium. The melanoma cell line MM200 was obtained as a gift from Peter Hersey (University of Newcastle) and A2058 was obtained as a gift from Dr Peter Parsons (QIMR). Both were cultured in DMEM medium.

All cultures were supplemented with 10% FCS (CSL, Australia), penicillin (100 U/ml), streptomycin (100 mg/ml), L-glutamine (2 mM) and sodium bicarbonate (1.2 g/L), and cultured at 37° C. in a humidified atmosphere of 5% $CO_2$. All cell lines were purchased from ATCC (Maryland, USA) except where noted.

The normal cell line NFF (neonatal foreskin fibroblasts) was a gift from Dr. Peter Parsons (Queensland Institute of Medical Research). RK (rabbit kidney) cells were obtained from Miller Whalley (Macquarie University). Both cell lines were cultured in RPMI supplemented with 10% FCS (CSL, Australia), penicillin (100 U/ml), streptomycin (100 mg/ml), L-glutamine (2 mM) and sodium bicarbonate (1.2 g/L), and cultured at 37° C. in a humidified atmosphere of 5% $CO_2$

2.2. Proliferation Assays

IC50 values were determined for each cell line. Cells were seeded in 96-well plates at an appropriate cell density as determined from growth kinetics analysis and cultured for 5 days in the absence and presence of the test compounds. Cell proliferation was assessed after the addition of 20 µl of 3-4,5 dimethylthiazol-2,5-diphenyl tetrazolium bromide (MTT, 2.5 mg/ml in PBS, Sigma) for 3-4 hrs at 37° C. according to manufacturer's instructions. IC50 values were calculated from semi-log plots of % of control proliferation on the y-axis against log dose on the x-axis.

2.3. Compound No. 1 Pharmacokinetics—Oral

Compound No. 1 labelled above in Example 1 was prepared as homogenous suspensions in 1% CMC(m:v, water). The formulation was delivered orally by gavage to female BALB/c mice at a dosage of 50 mg/kg. Three animals were allocated to each timepoint (15 min, 30 min, 1 hr, 4 hr and 24 hr). At each respective timepoint, animals were euthanased by cervical dislocation and blood collected. The concentration of free compound was analysed by mass spectroscopy.

3.0. Results
3.1. Normal Cell Toxicity.

Duplicate cutotoxicity assays against rabbit kidney cells demonstrated that compound No. 1 has mild toxicity against these cells (Table 1). When compared to cisplatin and phenoxodiol another benchmark against which potential anticancer drugs can be tested the degree of toxicity exhibited by compound No. 1 was greater than both the comparator compounds (2 µM compound No. 1 vs 9.9 µM cisplatin).

TABLE 1

Relative toxicity of compound No. 1 and cisplatin against rabbit kidney cells.

| Tissue/cell type | Designation | Analogue (IC50 uM) | | Antineoplastic (IC50 uM) Cisplatin |
|---|---|---|---|---|
| | | Phenoxodiol | Compound No. 1 | |
| Kidney | Rabbit Kidney | >150 | >60 | NT |
| Fibroblast | Neonatal Foreskin Fibroblasts (Human, NFF) | >150 | ~2 | 9.85 ± 5 |

3.2. In Vitro Efficacy Against Cancer Cells.

When compared the IC50 values of phenoxodiol and compound No. 1, were compared, compound No. 1 demonstrated superior activity (~2-10 fold greater) against the ovarian cancer cell line (CP70), the AR negative, p53 Mt prostate cancer cell line (PC3), ER negative (p53 mt) breast cancer cell line (MDA-MB-468 respectively), p53 Mt Glioma (HTB-138), and p53 Mt small cell lung cancer (Table 2). Compound No. 1 exhibited anti-cancer activity comparable to that of phenoxodiol against all other cell lines tested (Table 2) except HT-29 which is a colorectal cell line. Compound No. 1 was also equipotent against the melanoma cell line MM200 (Table 2.1).

Thus, compound No. 1 shows good anticancer activity against a broad range of cancer cell types, including ovarian, prostate, breast, glioma, pancreatic lung, colorectal and melanoma.

A number of cancer cell lines were tested against analogues of compound No. 1 and their IC50 values were compared. The results show that compound No. 1 is the best across a broad range of cell lines, whilst compound No. 20 also showed good results against ovarian, prostate breast leukaemia and melanoma cell lines. Compound Nos. 15 and 17 also showed good results against ovarian and melanoma cell lines respectively (Table 2.2).

TABLE 2.1

Comparison of compound No. 1 and Phenoxodiol cytoxicity against cell lines representative of different malignancies

| Indication | Cell line | Phenoxodiol | Compound No 1 |
|---|---|---|---|
| Ovarian | A2780 | 1.7 ± 0.61 | NT |
|  | CCP70 | 11.1 ± 23.6 | 1.7 |
| Prostate | PC3 | 9.1 ± 8 | 1.7 ± 0.5 |
| Breast | MDA-MB-468 | 8.9 ± 4.8 | 0.6 ± 0.01 |
| Glioma | HTB-138 | 20.4 ± 17.5 | 1.1 |
| Pancreatic | HPAC | 56.6 ± 16.8 | NT |
| Lung | NCI-H23 | 8.3 ± 6.7 | 1.9 ± 0.1 |
| Colorectal | HT-29 | 52.5 ± 19.5 | 17.44 |
| Melanoma | MM200 | 6.2 ± 4.5 | 1.0 ± 0.01 |

TABLE 2.2(a)

Comparison of compound Nos. 1, 10, 11, 12 and 14 to 20 cytoxicity against cell lines representative of different malignancies

| Indication | Cell line | Cpd. 14 | Cpd. 30 | Cpd. 11 | Cpd. 15 | Cpd. 27 | Cpd. 31 |
|---|---|---|---|---|---|---|---|
| Ovarian | CP70 | 61.3 | 18 | 52.7 ± 13 | 65 ± 1.9 | 22.4 ± 0.7 | 53.4 |
| Prostate | PC3 | 74 ± 4 | 45 ± 4.9 | >100 | >100 | 28 ± 7.3 | 47 ± 8.4 |
| Breast | MDA-MB-468 | >100 | >100 | NT | NT | NT | NT |
| Glioma | HTB-138 | >100 | 45.7 | 86.3 | >100 | 33.7 | 94.6 |
| Pancreatic | HPAC | >100 | 41 ± 5.3 | >100 | >100 | 27.6 ± 5.3 | 34.6 |
| leukaemia (ALL) | CCRF-CEM | 90.2 | 66.6 | 95.4 | 81.8 | 16.6 | 51.5 ± 12 |
| NSC Lung | NCI-H460 | >100 | 43.5 ± 9.2 | >100 | >100 | 31.6 ± 4.9 | 76.3 |
| Colorectal | HT-29 | NT | NT | NT | NT | NT | >100 |
| Melanoma | MM200 | 72.8 | 33 ± 3 | 60.4 ± 9.2 | NT | 14.6 | 27.2 ± 4.6 |

TABLE 2.2(b)

Comparison of compound Nos. 1, 10, 11, 12 and 14 to 20 cytoxicity against cell lines representative of different malignancies

| Indication | Cell line | Cpd. 10 | Cpd. 12 | Cpd. 28 | Cpd. 32 | Cpd. 1 |
|---|---|---|---|---|---|---|
| Ovarian | CP70 | 27.5 | >100 | 62 ± 44 | 17.7 ± 5.9 | 1.9 ± 0.4 |
| Prostate | PC3 | 37.5 ± 0.4 | 32.8 ± 4.7 | 49 ± 16 | 13 ± 0.6 | 1.6 ± 0.8 |
| Breast | MDA-MB-468 | NT | 63.5 ± 4.6 | 30.5 ± 4 | 9.2 ± 5.1 | 1 ± 0.6 |
| Glioma | HTB-138 | 60.2 | 47.7 | 62.4 | 29 ± 2 | 1.16 |
| Pancreatic | HPAC | 50 | 86.3 ± 67 | 50.7 ± 35 | 35.8 | 51.7 ± 8 |
| leukaemia (ALL) | CCRF-CEM | 40.7 | >100 | >100 | 15.4 | 1.6 ± 1.2 |
| NSC Lung | NCI-H460 | 39.7 | NT | 41.6 | 39.3 ± 7.7 | 1.2 ± 0.45 |
| Colorectal | HT-29 | NT | 49.5 ± 32 | 29.4 ± 4.4 | 24.8 ± 3.9 | 15.7 ± 2.4 |
| Melanoma | MM200 | NT | >100 | 64 ± 74 | 12.6 ± 3.7 | 0.78 ± 0.23 |

3.3. Compound No. 1 Pharmacokinetics—Oral

Oral pharmacokinetics was determined in the female BALB/c mouse. A Cmax of 27.3 μM free compound No. 1 was observed in the sera 15 minutes post administrations. Compound No. 1 was rapidly eliminated from sera with a concentration of 8.2 μM observed after 30 min and 2.4 μM after 1 hr making the half life of this agent around 30 minutes (FIG. 1 and Table 3). The majority of compound No. 1 in sera was present in its conjugated state with the concentration of total compound No. 1 (free plus conjugate) achieved being ~100 μM 15 min post administration (1:4; free:total). The ratio of free:total decreased over time (1:12 after 30 min and 1:13 after 1 hr). Rapid appearance of compound No. 1 in urine at high concentrations (815 μM) 15 min post administration provides evidence that compound No. 1 is absorbed from the gastro intestinal tract and excreted via the kidneys.

Compound No. 1 concentrations in urine peaked at 30 min (2640 μM) with levels declining to ~1500 μM and 545 μM at 1 and 4 hr respectively post administration. The majority of said compound was present in it's conjugated form with only ≦2% as the free entity was noted at any time-point. A large proportion of said compound was also excreted in faeces, which was observed at least 1 hr post administration. However, it is not possible to confirm whether hepatic excretion is a mode of removal for this compound due to the fact that no liver samples were assessed and because the observation of the compound in faeces may be due to residual compound powder not absorbed from the gastro intestinal tract. It is interesting to note that almost 100% of the compound recovered from faeces was present in it's free form.

4.0. Effect on Murine Macrophages (RAW 264.7) Stimulated with LPS

The mouse macrophage cell line RAW 264.7 was cultured in DMEM supplemented with foetal calf serum (FCS), 2 mM glutamine and 50 U/ml penicillin/streptomycin. Subconfluent cells were detached from the flask by gentle scraping and 24-well plates seeded at $5 \times 10^5$ cells per well and allowed to adhere for 1 hr. Cells were then treated either test compound at a concentration of 10 μM (in 0.025% DMSO) or vehicle alone, and incubated for 1 hr. LPS 50 ng/ml (LPS -Sigma-Aldrich) was then added. After incubation for 16 hrs, culture media was collected and stored at −80° C. for ecosanoid measurements using enzyme immunometric assays ($PGE_2$ and $TXB_2$—Cayman Chemical).

TABLE 5

Percentage change in eicosanoid synthesis after incubating test compound at 10 μM compared with incubation with vehicle alone.

| Compound | $PGE_2$ | $TXB_2$ |
|---|---|---|
| 1 | −53.8 | −15.9 |
| 14 | −23.6 | −40.9 |
| 30 | −60.7 | −62.6 |
| 11 | −51.0 | −53.2 |
| 15 | −38.3 | −58.4 |
| 27 | −84.2 | −86.1 |
| 31 | −41.4 | −48.3 |
| 10 | −23.1 | −7.1 |
| 12 | −68.3 | −34.0 |
| 28 | −85.1 | −50.1 |
| 32 | −71.1 | −34.4 |

Positive values indicate enhanced synthesis; negative values indicate inhibition of synthesis and consequently suggest anti-inflammatory activity.

TABLE 3

Compound No. 1 pharmacokinetics and distribution in serum, faeces and urine.

| | Compound No. 1 Concentration | | | | | | | | |
|---|---|---|---|---|---|---|---|---|---|
| Time (days) | Serum Free (uM) | Serum Total (uM) | % Free | Faeces Free (uM) | Faeces Total (uM) | % Free | Urine Free (uM) | Urine Total (uM) | % Free |
| 0.25 | 27.3 ± 23 | 103.4 ± 36.5 | 26.4 | | | | 17.1 ± 7.2 | 815 ± 268 | 2.1 |
| 0.5 | 8.2 ± 6.5 | 77.2 ± 8 | 10.6 | | | | 22.1 ± 1.5 | 2640 ± 1190 | 0.8 |
| 1 | 2.4 ± 1.6 | 31.4 ± 9.4 | 7.6 | 1055 ± 913 | 1067 ± 924 | 98.9 | 26.3 ± 2.2 | 1535 ± 158 | 1.7 |
| 4 | 0.3 ± 0.02 | 5.2 ± 0.8 | 5.8 | 1792 ± 625 | 1861 ± 630 | 96.3 | 1.1 ± 0.1 | 545 ± 203 | 0.2 |
| 24 | 0.05 ± 0.02 | 0.56 ± 0.5 | 8.9 | 800 ± 670 | 815 ± 680 | 98.2 | 0.1 ± 0.1 | 7.04 ± 3.6 | 1.4 |

Data are representative of Average ± SEM.

When compared to the oral pharmacokinetic data of phenoxodiol and compound No. 1 would appear to have a similar half life, however 10-20 fold higher free concentrations of compound No. 1 were achieved after 15 and 30 min. Approximately 2-fold higher concentrations were observed after 1 hr.

TABLE 4

Comparative oral pharmacokinetic data for Compound No. 1 and Phenoxodiol.

| | Compound No. 1 (uM) | | Phenoxodiol (uM) | |
|---|---|---|---|---|
| Time | Free | Total | Free | Total |
| 0.25 | 27.3 ± 23 | 103 ± 36.5 | 3.3 ± 0.13 | 511.5 ± 99 |
| 0.5 | 8.2 ± 6.5 | 77.2 ± 8 | 2.9 ± 0.05 | 357 ± 82 |
| 1 | 2.4 ± 1.6 | 31.3 ± 9.4 | 1.5 ± 0.11 | 387 ± 22.8 |
| 4 | 0.33 ± 0.02 | 5.2 ± 0.7 | 1.3 ± 0.07 | 117.6 ± 42 |
| 24 | 0.05 ± 0.02 | 0.56 ± 0.49 | 0.15 ± 0.04 | 0.13 ± 0.1 |
| Dose* | 13.8 mg/ml | | 4.6 mg/ml | |

5.0 Conclusions

Compound No. 1 exhibits marked toxicity toward primary explants of non-transformed neonatal foreskin fibroblasts at concentrations less than cisplatin (IC50=2 μM compound No. 1 vs 9 μM cisplatin respectively). However, relative mild toxicity was noted against rabbit kidney cells (Compound No. 1 IC50>60 μM). Efficacy studies demonstrate that compound No. 1 is active against cell lines representative of melanoma (MM200) and glioma (HTB-128). However, compound seems particularly active against cell lines representative of prostate (PC3), breast (MDA-MB-468) and lung cancer (NCIHH-H23) which traditionally have been cancers which are very difficult to treat.

Compound No. 1 was moderately active against the colorectal cell line HT-29.

Pharmacokinetic analysis of compound No. 1 revealed that oral administration of the drug yields markedly higher concentrations of the free form of the drug when compared to similarly administered phenoxidiol at 15 and 30 min post administration. Compound No. 1 and phenoxodiol each exhibit similar t1/2 (~30 min).

Preliminary formulation studies of compound No. 1 reveal that the molecule has moderate to low solubility in 20% HPBCD (11.2 mg/ml).

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited herein, if any, are hereby incorporated by reference.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

SELECTED REFERENCE ARTICLES

Constantinou A I, Mehta R, Husband A. 2003 Phenoxodiol, a novel isoflavone derivative, inhibits dimethylbenz[a]anthracene (DMBA)-induced mammary carcinogenesis in female Sprague-Dawley rats. Eur J Cancer. 39, 1012-8.

Constantinou A I, Husband A. 2002 Phenoxodiol (2H-1-benzopyran-7-0,1,3-(4-hydroxyphenyl)), a novel isoflavone derivative, inhibits DNA topoisomerase II by stabilizing the cleavable complex. Anticancer Res. 22, 2581-5.

Gamble, J R., Xia, P., Hahn, C., Drew, J., Drogemuller, C., Carter, C., Walker, C., Brown, D M., Vadas, M A. 2003 Phenoxodiol, a derivative of plant flavanoids, shows potent anti-tumour and anti-angiogenic properties. Nature Medicine. Submitted.

Hersey, P and Zhang, X. D. 2001 How melanoma cells evade Trail-induced apoptosis. Nature reviews, Cancer, 1, 142-150.

Kamsteeg, M., Rutherford, T., Sapi, E., Hanczaruk, B., Shahabi, S., Flick, M., Brown, D. M and Mor, G. 2003 Phenoxodiol—an isoflavone analogue—induces apoptosis in chemo-resistant ovarian cancer cells. Oncogene, 22, 2611-20.

The invention claimed is:

1. A method for the treatment of cancer or a tumour mass, which comprises administering to a subject in need thereof a therapeutically effective amount of a compound of formula (I-b):

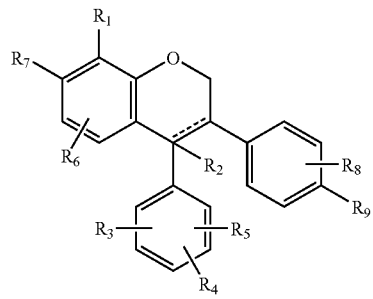

wherein:

$R_1$ is $C_{1-6}$ alkyl;

the drawing "---" and $R_2$ together represent a double bond or the drawing "---" represents a single bond and $R_2$ is hydrogen or hydroxy, $R_3$, $R_4$ and $R_5$ are independently hydrogen, hydroxy, halo, $NR_{10}R_{11}$, $C_{1-6}$ alkoxy, $C_{1-6}$ fluoroalkyl or $C_{1-6}$ alkyl;

$R_6$ is hydrogen;

$R_7$ is hydroxy or $C_{1-6}$ alkoxy;

$R_8$ and $R_9$ are independently hydrogen, hydroxy, halo, $NR_{10}R_{11}$, $C_{1-6}$ alkoxy, $C_{1-6}$ fluoroalkyl or $C_{1-6}$ alkyl; and $R_{10}$ and $R_{11}$ are independently hydrogen, $C_{1-6}$ alkyl or trialkyl silyl.

2. The method of claim 1, wherein the compound of formula (I-b) is selected from compound Nos. 1 to 9 as set forth below:

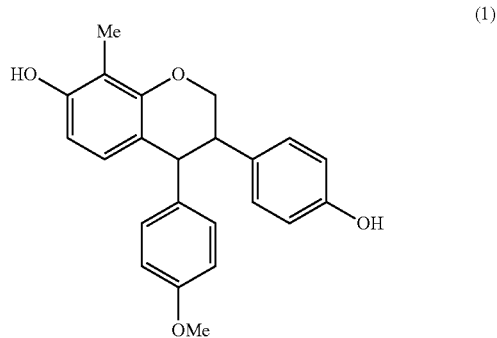

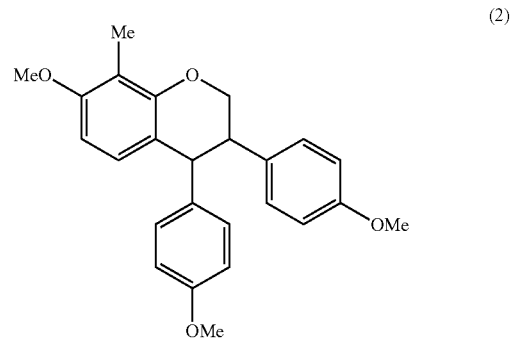

(3)
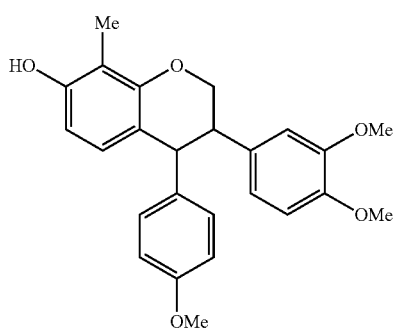

(4)
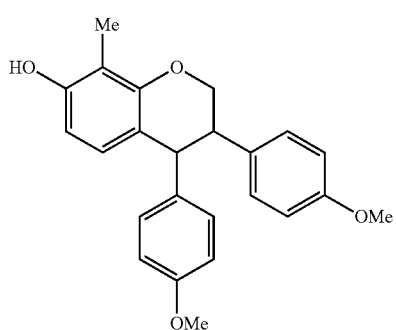

(5)
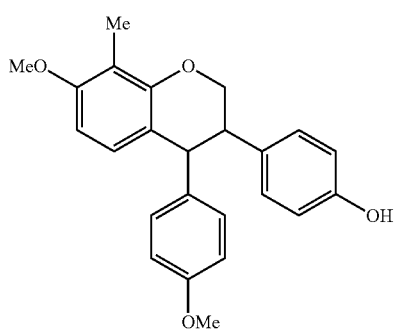

(6)
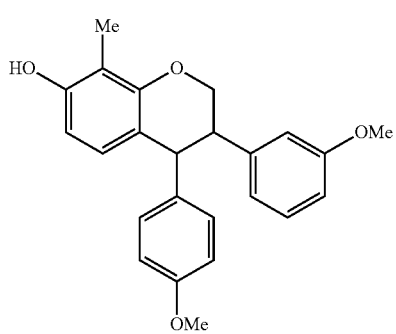

(7)
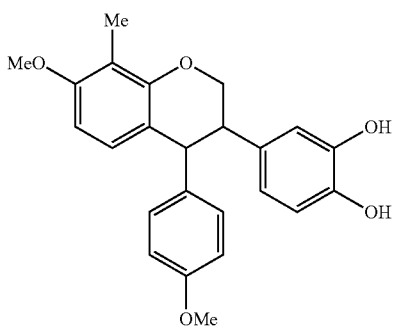

(8)
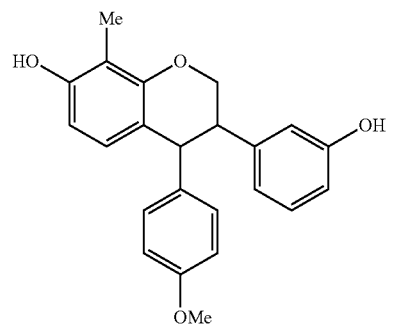

(9)
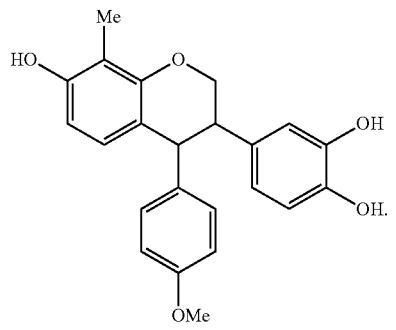

3. The method of claim 1, wherein the cancer or tumour mass is of epithelial origin, of mesenchymal origin or of neural origin.

4. The method of claim 3, wherein the cancer or tumour mass of epithelial origin is prostate, ovarian, cervical, breast, gall-bladder, pancreatic, colorectal, renal or non-small lung cancer.

5. The method of claim 3, wherein the cancer or tumour mass of mesenchymal origin is melanoma, mesothelioma or sarcoma cancer.

6. The method of claim 3, wherein the cancer or tumour mass of neural origin is glioma.

7. The method of claim 1, wherein the compound is simultaneously administered with an anti-cancer agent.

8. The method of claim 1, wherein the compound is sequentially administered with an anti-cancer agent.

9. The method of claim 7, wherein the anti-cancer agent is cisplatin, dehydroequol or paclitaxel.

10. The method of claim 8, wherein the anti-cancer agent is cisplatin, dehydroequol or paclitaxel.

11. The method of claim 7, wherein the compound of formula (I-b) is:

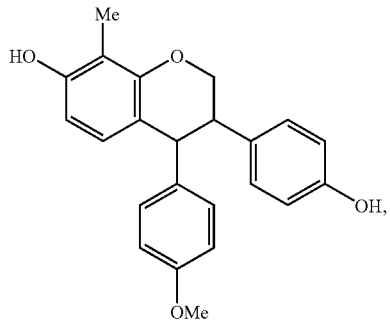

(1)

said anti-cancer agent is dehydroequol, and said subject is afflicted with ovarian or pancreatic cancer.

12. The method of claim 8, wherein the compound of formula (I-b) is:

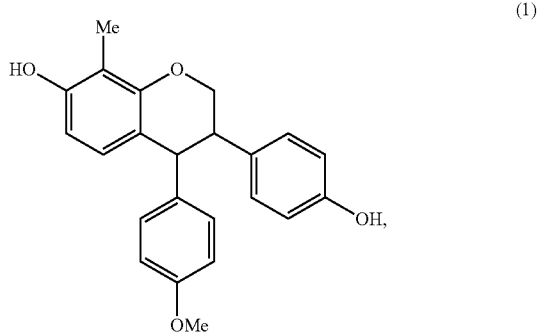

(1)

said anti-cancer agent is dehydroequol, and said subject is afflicted with ovarian or pancreatic cancer.

13. The method of claim 1, wherein the compound acts as a chemosensitising agent.

* * * * *